United States Patent
Godeau et al.

(10) Patent No.: US 9,878,016 B2
(45) Date of Patent: Jan. 30, 2018

(54) IGFBP-3 DERIVATIVES AND USES THEREOF

(71) Applicants: Jean-Francois Godeau, Paris (FR); Yves Le Bouc, Paris (FR)

(72) Inventors: Jean-Francois Godeau, Paris (FR); Yves Le Bouc, Paris (FR)

(73) Assignee: INSERM (Institut National de la Sante et de la Recherche Medicale), Paris (FR)

( * ) Notice: Subject to any disclaimer, the term of this patent is extended or adjusted under 35 U.S.C. 154(b) by 0 days.

(21) Appl. No.: 14/750,346

(22) Filed: Jun. 25, 2015

(65) Prior Publication Data

US 2015/0290297 A1 Oct. 15, 2015

Related U.S. Application Data

(63) Continuation of application No. 14/001,077, filed as application No. PCT/EP2012/053142 on Feb. 24, 2012, now abandoned.

(30) Foreign Application Priority Data

Feb. 24, 2011 (EP) .................................... 11305197

(51) Int. Cl.
*C07K 14/47* (2006.01)
*A61K 38/30* (2006.01)
*C07K 14/71* (2006.01)
*C07K 16/28* (2006.01)
*G01N 33/74* (2006.01)

(52) U.S. Cl.
CPC .......... *A61K 38/30* (2013.01); *C07K 14/4743* (2013.01); *C07K 14/71* (2013.01); *C07K 16/2863* (2013.01); *G01N 33/74* (2013.01); *G01N 2333/65* (2013.01)

(58) Field of Classification Search
None
See application file for complete search history.

(56) References Cited

U.S. PATENT DOCUMENTS

2006/0153853 A1  7/2006  Forbes

FOREIGN PATENT DOCUMENTS

| EP | 0965596 A1 | 12/1999 |
|---|---|---|
| WO | 99/63086 A2 | 12/1999 |
| WO | 2002034916 A2 | 5/2002 |
| WO | 2004/007543 A1 | 1/2004 |
| WO | 2004007543 A1 | 1/2004 |
| WO | 2005/049648 A2 | 6/2005 |

OTHER PUBLICATIONS

InvivoGen, "IgG-Fc Engineering for therapeutic use," InvivoGen Insight pp. 1-4 (Apr./May 2006).*
Bara et al., "Gastric M1 Mucin, An Early Oncofetal Marker of Colon Carcinogenesis, Is Encoded by the MUC5AC Gene," Int. J. Cancer 75:767-773 (1998).*
Baxter R. C., et al., "Modulation of Human IGF Binding Protein-3 Activity by Structural Modification", Progress in Growth Factor Research, Jan. 1, 1995, pp. 215-222, vol. 6, No. 2-04, Pergamon Press, Great Briton.
Jones J. I., et al., "Insulin-Like Growth Factors and Their Binding Proteins: Biological Actions", Endocrine Reviews, Feb. 1, 1995, pp. 3-34, vol. 16, No. 1, Baltimore, MD, US.
Hashimoto R., et al., "Binding sites and binding properties of binary and ternary complexes of insulin-like growth factor-II (IGF-II), IGF-binding protein-3, and acid-labile subunit", The Journal of Biological Chemistry, Oct. 31, 1997, pp. 27936-27942, vol. 272, No. 44, USA.
Kubler B., et al., "Isolation and Characterization of circulating fragments of the insulin-like growth factor binding protein-3", FEBS Letters, May 8, 2002, pp. 124-128, vol. 518, No. 1-3, Elsevier, Amsterdam.
R. Clay Bunn, et al., "Insulin-like growth factor binding protein proteolysis", Trends in Endocrinology & Metabolism, May 1, 2003, pp. 176-181, vol. 14, No. 4, Elsevier.
Villegas R. L., et al., "Development of Non-Viral Gene Therapy Targeting Insulin-Like Growth Factor (IGF) System for Treatment of Brain Tumors", Molecular Therapy, Jan. 1, 2006, p. S358, vol. 13, Academic Press, San Diego, CA, US.
Monalisa S., et al., "Insulin-Like Growth Factor System in HIV/AIDS: A Structure Based Approach to the Design of New Therapeutics, HIV and AIDS—Updates on Biology, Immunology, Epidemiology and Treatment Strategies", Oct. 26, 2011, pp. 125-142, India.
UniProtKP/Swiss-Prot Accession No. P17936 (accessed Sep. 2, 2014 at URL uniprot.org/uniprot/P17936, last sequence update Mar. 6, 2007).
Fowlkes et al.; "Matrix Metalloproteinases Degrade Insulin-like Growth Factor-binding Protein-3 in Dermal Fibroblast Cultures"; J. Biol. Chem, 269, 1994, pp. 25742-25746.
Cull et al.; "Biotinylation of proteins in vivo and in vivo using small peptide tags"; Meth. Enz. 326, 2000, pp. 430-440.

* cited by examiner

*Primary Examiner* — Julie Ha
*Assistant Examiner* — Kristina M Hellman
(74) *Attorney, Agent, or Firm* — Whitham, Curtis & Cook, P.C.

(57) ABSTRACT

The present invention provides polypeptide derivatives of IGFBP-3 that are resistant to proteolytic cleavage. These IGFBP-3 derivatives are useful in a variety of therapeutic and diagnostic applications. Also provided are pharmaceutical compositions and kits comprising such IGFBP-3 derivatives and methods for using these derivatives for the treatment of a variety of disorders.

17 Claims, 13 Drawing Sheets

Coomassie blue staining       Western transert Streptavidin-HRP

A

B

C

A

B

A

B

SEQUENCE LISTING

<160> NUMBER OF SEQ ID NOS: 16

<210> SEQ ID NO 1
<211> LENGTH: 114
<212> TYPE: PRT
<213> ORGANISM: Homo sapiens

<400> SEQUENCE: 1

Met Gln Arg Ala Arg Pro Thr Leu Trp Ala Ala Leu Thr Leu Leu
1               5                   10                  15

Val Leu Leu Arg Gly Pro Pro Val Ala Arg Ala Gly Ala Ser Ser Ala
                20                  25                  30

Gly Leu Gly Pro Val Val Arg Cys Glu Pro Cys Asp Ala Arg Ala Leu
            35                  40                  45

Ala Gln Cys Ala Pro Pro Ala Val Cys Ala Glu Leu Val Arg Glu
    50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys Gly Ser Gly Leu Arg Cys Gln Pro
                85                  90                  95

Ser Pro Asp Glu Ala Arg Pro Leu Gln Ala Leu Leu Asp Gly Arg Gly
            100                 105                 110

Leu Cys

<210> SEQ ID NO 2
<211> LENGTH: 98
<212> TYPE: PRT
<213> ORGANISM: Homo sapiens

<400> SEQUENCE: 2

Val Asn Ala Ser Ala Val Ser Arg Leu Arg Ala Tyr Leu Leu Pro Ala
1               5                   10                  15

Pro Pro Ala Pro Gly Asn Ala Ser Glu Ser Glu Glu Asp Arg Ser Ala
                20                  25                  30

Gly Ser Val Glu Ser Pro Ser Val Ser Ser Thr His Arg Val Ser Asp
            35                  40                  45

Pro Lys Phe His Pro Leu His Ser Lys Ile Ile Ile Ile Lys Lys Gly
        50                  55                  60

His Ala Lys Asp Ser Gln Arg Tyr Lys Val Asp Tyr Glu Ser Gln Ser
65                  70                  75                  80

Thr Asp Thr Gln Asn Phe Ser Ser Glu Ser Lys Arg Glu Thr Glu Tyr
                85                  90                  95

Gly Pro

<210> SEQ ID NO 3
<211> LENGTH: 79
<212> TYPE: PRT
<213> ORGANISM: Homo sapiens

<400> SEQUENCE: 3

Cys Arg Arg Glu Met Glu Asp Thr Leu Asn His Leu Lys Phe Leu Asn
1               5                   10                  15

Val Leu Ser Pro Arg Gly Val His Ile Pro Asn Cys Asp Lys Lys Gly
                20                  25                  30

Phe Tyr Lys Lys Lys Gln Cys Arg Pro Ser Lys Gly Arg Lys Arg Gly
            35                  40                  45

Phe Cys Trp Cys Val Asp Lys Tyr Gly Gln Pro Leu Pro Gly Tyr Thr

```
                50                  55                  60
Thr Lys Gly Lys Glu Asp Val His Cys Tyr Ser Met Gln Ser Lys
 65                  70                  75

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide linker

<400> SEQUENCE: 4

Gly Gly Gly Ser Gly Gly Ser Gly Gly Ser Gly Gly Ser Gly Gly
 1               5                  10                  15

<210> SEQ ID NO 5
<211> LENGTH: 5
<212> TYPE: PRT
<213> ORGANISM: Artificial Sequence
<220> FEATURE:
<223> OTHER INFORMATION: Synthetic ALS non binding site

<400> SEQUENCE: 5

Ala Gly Gly Ser Gly
 1               5

<210> SEQ ID NO 6
<211> LENGTH: 15
<212> TYPE: PRT
<213> ORGANISM: Artificial Sequence
<220> FEATURE:
<223> OTHER INFORMATION: Synthetic BirA enzyme substrate

<400> SEQUENCE: 6

Gly Leu Asn Asp Ile Phe Glu Ala Gln Lys Ile Glu Trp His Glu
 1               5                  10                  15

<210> SEQ ID NO 7
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 7
atcgaaggcc gtgggggcca gggcgcgagc tcggggggct ggg                         44

<210> SEQ ID NO 8
<211> LENGTH: 52
<212> TYPE: DNA
<213> ORGANISM: Artificial Sequence
<220> FEATURE:
<223> OTHER INFORMATION: Synthetic oligonucleotide primer

<400> SEQUENCE: 8
cctcgagtta tcagctgccc ttgctctgca tgctgtagca gtgcacgtcc tc              52

<210> SEQ ID NO 9
<211> LENGTH: 84
<212> TYPE: DNA
<213> ORGANISM: Artificial Sequence
<220> FEATURE:
<223> OTHER INFORMATION: Synthetic mutagenic oligonucleotide

<400> SEQUENCE: 9
gggaccatat tctgtctcac caccagaccc gccagacccg ccagacccgc cagacccgcc      60
```

```
accgctgacg gcactagcgt tgac                                              84

<210> SEQ ID NO 10
<211> LENGTH: 50
<212> TYPE: DNA
<213> ORGANISM: Artificial Sequence
<220> FEATURE:
<223> OTHER INFORMATION: Synthetic mutagenic oligonucleotide

<400> SEQUENCE: 10
ccacacacca gcagaagccg ccgctgccgc ccgcggaagg gcgacactgc                  50

<210> SEQ ID NO 11
<211> LENGTH: 76
<212> TYPE: DNA
<213> ORGANISM: Artificial Sequence
<220> FEATURE:
<223> OTHER INFORMATION: Synthetic mutagenic oligonucleotide

<400> SEQUENCE: 11
cccctcgagt cattattcgt gccattcaat tttttgggct tcaaaaatgt cgttcaggcc       60
gctgcccttg ctctgc                                                      76

<210> SEQ ID NO 12
<211> LENGTH: 5
<212> TYPE: PRT
<213> ORGANISM: Artificial Sequence
<220> FEATURE:
<223> OTHER INFORMATION: Synthetic sequence

<400> SEQUENCE: 12

Lys Gly Arg Lys Arg
1               5

<210> SEQ ID NO 13
<211> LENGTH: 18
<212> TYPE: PRT
<213> ORGANISM: Artificial Sequence
<220> FEATURE:
<223> OTHER INFORMATION: hexa-histidine purification sequence

<400> SEQUENCE: 13

Ile Ile Leu Val Pro Arg Gly Ser His His His His His His Ile Glu
1               5                   10                  15

Gly Arg

<210> SEQ ID NO 14
<211> LENGTH: 7
<212> TYPE: PRT
<213> ORGANISM: Artificial Sequence
<220> FEATURE:
<223> OTHER INFORMATION: Artificial peptide

<400> SEQUENCE: 14

Val Asn Ala Ser Ala Val Ser
1               5

<210> SEQ ID NO 15
<211> LENGTH: 6
<212> TYPE: PRT
<213> ORGANISM: Artificial Sequence
<220> FEATURE:
<223> OTHER INFORMATION: Artificial peptide

<400> SEQUENCE: 15
```

```
Glu Thr Glu Tyr Gly Pro
1               5

<210> SEQ ID NO 16
<211> LENGTH: 15
<212> TYPE: PRT
<213> ORGANISM: Artificial Sequence
<220> FEATURE:
<223> OTHER INFORMATION: Synthetic AviTag - substrate for the BirA
      enzyme

<400> SEQUENCE: 16

Gly Leu Asn Asp Ile Phe Glu Ala Gln Lys Ile Glu Trp His Glu
1               5                   10                  15
```

IGFBP-3 DERIVATIVES AND USES THEREOF

RELATED APPLICATION

The present application is a continuation of U.S. patent application Ser. No. 14/001,077 filed Sep. 18, 2013, which is a 371 national stage application based on PCT/EP2012/053142 filed Feb. 24, 2012, which claims priority to European Patent Application No. EP 11 305 197.3 filed on Feb. 24, 2011, which is incorporated herein by reference in its entirety.

BACKGROUND OF THE INVENTION

The IGF (insulin-like growth factor) system consists of a well characterized set of polypeptides that cells use to communicate with their physiologic environment. This system comprises two cell-surface receptors (IGF1R and IGF2R), two peptidic ligands (IGF-I and IGF-II), a family of six high-affinity IGF binding proteins (IGFBP-1 to 6), as well as associated IGFBP-degrading enzymes, referred to collectively as proteases. The IGF signalling pathway is not only a major player in mammalian statural growth but is also involved in cellular proliferation and survival. Even though growth hormone (GH) is the primary regulator of IGF-I production in many tissues, IGFs are produced almost ubiquitously and circulate at high concentrations in serum mostly bound to IGFPBs. For IGFs to exert their effects through association with IGF1R, their tyrosine kinase cell-surface receptor, they must first dissociate from the complexes formed with IGFBP whose affinities for IGF-I and IGF-II are sometimes higher than those of IGF1R. Thus, receptor-ligand interaction is highly dependent on "free" IGF levels which are tightly regulated by the IGFBPs present in serum and other biological fluids. Therefore, the interaction of IGFs with IGFBPs can prevent untoward IGF effects, such as uncontrolled cellular proliferation or hypoglycaemia. Conversely, disruption of the IGF/IGFBP complex is a probable prerequisite for IGFs to exert their mitogenic and metabolic effects through the IGF receptor.

Dysregulated IGF signalling pathway has emerged as a major player in the pathogeny of numerous malignant tumors as well as in their resistance to chemotherapeutic agents (Samani et al., Endocr. Rev., 2006, 24: 24). Increased activity in this pathway promotes cell proliferation via the activation of the Ras/MAPK/ERK pathway, and counteracts pro-apoptotic signals through the activation of the PI3-kinase signalling pathway. For these reasons, targeting the IGF signalling pathway in order to reduce its activity has become a major challenge of current medical research (Yuen and Macaulay, Expert. Opin. Ther. Targets, 2008, 12: 589-603).

Furthermore, modifying the IGF supply to certain tissues could help control the course of a wide variety of human diseases including dwarfism due to IGF deficiency, type I and type II diabetes, but also degenerative diseases such as myotonic muscular dystrophy (Heatwole et al., Arch. Neurol., 2011, 68: 37-44), amyotrophic lateral sclerosis neurodegeneration (Goberdhan et al., Differentiation, 2003, 71: 375-397) and vasculo-proliferative retinopathies such as those complicating diabetes, prematurity and ageing and even arteriosclerosis. In addition, an acute increase in bio-available IGF may be beneficial to patients suffering from burns, brain or heart ischemia, wasting syndromes and losses of bone mineral density (Clemmons, Nat. Rev. Drug Discov., 2007, 6: 821-833).

The concentrations of IGF-I and IGF-II in the blood are, at least in part, indirectly determined by the levels of IGFBPs. The insulin-like growth factor binding protein 3 (IGFBP-3) is the most abundant IGFBP in blood and has the highest affinity for IGF-I and IGF-II and is, therefore, the main IGF reservoir in the blood stream (Jones and Clemmons, Endocr. Rev., 1995, 16: 3-34). In addition to its role in IGF sequestration and transport, IGFBP-3 may have biological effects of its own. In line with its five IGFBP congeners, IGFBP-3 consists of three domains of roughly equal size of which only the N-terminal and C-terminal domains participate in IGF binding (Sitar et al., Proc. Natl. Acad. Sci. USA, 2006, 103: 13028-13033). The intermediate domain, which is loosely structured, is the target of proteolytic cleavages crucial to some of its functions (Fowlkes et al., Endocrinology, 2004, 145: 620-626). IGFBP-degrading proteases induce the release of IGF, from IGF/IGFBP-3 complexes, making IGF available for biological action. In addition, certain free IGFBPs can also be acted upon by proteases, resulting in reduced affinity for IGFs.

Several approaches have been used to target the IGF signalling pathway including (1) reduction of IGF-1 levels or bioactivity using ligand-specific antibodies (Goya et al., Cancer Res., 2004, 64: 6252-6258) or growth hormone (GH) antagonists (Divisova et al., Breast Cancer Res. Treat., 2006, 98: 315-327) and (2) inhibition of IGF receptor function using (a) receptor-specific antibodies such as the anti-IGF1R antibodies developed by Pfizer (CP-751871—Lacy et al., J. Clin. Oncol., 2008, 26: 3196-3203; Haluska et al., Clin. Cancer Res., 2007, 13: 5834-5840; De Bono et al., Clin. Cancer Res., 2007, 13: 3611-3616), Amgen (AMG479—Tolcher et al., J. Clin. Oncol., 2007, 25: 3002; Sarantopoulos et al., J. Clin. Oncol., 2008, 26: 3583)), Sanofi-Aventis (AVE1642—Tolcher et al., J. Clin. Oncol., 2008, 25: 3582), Imclone (A12—Higano et al., J. Clin. Oncol., 2007, 25: 3505), Merck (MK0646—Hidalgo et al., J. Clin. Oncol., 2008, 26: 3520; Atzori et al., J. Clin. Oncol., 2008, 26: 3519) and Roche (R1507—Rodon et al., J. Clin. Oncol., 2007, 26: 3590) or (b) small-molecule tyrosine kinase inhibitors (Haluska et al., Cancer Res., 2006, 66: 362-371; Ji et al., Mol. Cancer Ther., 2007, 6: 2158-2167; Zimmermann et al., Bioorg. Med. Chem. Lett., 2008, 18: 4075-4080; Mulvihill et al., Bioorg. Med. Chem. Lett., 2008, 16: 1359-1375; Hofmann et al., Drug Discov. Today, 2005, 10:1041-1047; Vasilcanu et al., Oncogene, 2008, 27: 1629-1638).

Administration of recombinant IGF-I (called mecasermin, brand name: Increlex™ by Tercica, Inc.), when indicated, is hampered with undesired side effects such as hypoglycaemia, the short half life of free IGF-I and at the same time reduced efficacy due to endogenous IGFBPs. In an attempt to increase half-life while reducing these side effects of recombinant human IGF-1 (rhIGF-1), an approach consisting of administration of a complex made of equimolar amounts rhIGF-1 and recombinant human IGFBP-3 (rhIGFBP-3) (mecasermin rinfabate, brand name: SomatoKine™ or Iplex™ by Insmed Corp.) has been developed. The efficacy of the rhIGF-1/rhIGFBP-3 complex has been tested in subjects with severe-insulin resistance (Regan et al., J. Clin. Endocrinol. Metab., May 2010, 95: 2113-2122), growth-hormone insensitivity syndrome (Kemp et al., Endocr. & Metabol., 2006, 15: 409-415; Tonella et al., Horm. Res. Paediatr., February 2010, 73: 140-147), type 1 diabetes (Clemmons et al., J. Clin. Endocrin. Metab., 2000, 85: 1518-1524), type 2 diabetes (Clemmons et al., J. Clin. Endocrin. Metab., 2005, 90: 6561-6568), osteoporosis (Boonen et al., Endocrinol. Metab., 2002, 87: 1593-1599), burns (Jeschke et al., Mol. Med., 2002, 8: 238-246), myotonic dystrophy type 1 (Heatwole et al., Arch. Neurol., September 2010), as well as in low birth children (Iniguez et al., Clin. Endocrinol., 2006, 65: 687-392).

These studies are encouraging in that they demonstrate the usefulness of this approach to deliver IGF-I for therapeutic purposes.

SUMMARY OF THE INVENTION

The present invention relates to derivatives of IGFBP-3 that are useful in a variety of therapeutic and/or diagnostic applications.

In particular, in one aspect, the present invention provides IGFBP-3 derivatives which are resistant to proteolytic cleavage and which display binding affinities for IGF-I, IGF-II, heparin and ALS (Acid Labile Subunit) that are identical or substantially similar to the corresponding binding affinities of wild-type IGFBP-3.

More specifically, the present invention provides an IGFBP-3 polypeptidic derivative comprising an N-terminal domain, an intermediary domain and a C-terminal domain, wherein: (i) the N-terminal domain comprises the amino acid sequence of the N-terminal domain of wild-type IGFBP-3, of a biologically active variant thereof or of a biologically active fragment thereof; (ii) the intermediary domain comprises a linker resistant to proteolytic cleavage; and (iii) the C-terminal domain comprises the amino acid sequence of the C-terminal domain of wild-type IGFBP-3, of a biologically active variant thereof or of a biologically active fragment thereof.

In certain embodiments, the intermediary domain of the IGFBP-3 polypeptide derivative comprises, or alternatively consists of, the amino acid sequence of the intermediary domain of wild-type IGFBP-3, wherein a portion of said amino acid sequence is replaced with the linker resistant to proteolytic domain.

In certain embodiments, the IGFBP-3 is human IGFBP-3 and: (i) the amino acid sequence of the N-terminal domain of wild-type IGFBP-3 is as set forth in SEQ ID NO: 1; (ii) the amino acid sequence of the intermediary domain of wild-type IGFBP-3 is as set forth in SEQ ID NO: 2; and (iii) the amino acid sequence of the C-terminal domain of wild-type IGFBP-3 is as set forth in SEQ ID NO: 3.

In certain embodiments, the linker resistant to proteolytic cleavage has the sequence set forth in SEQ ID NO: 4 or any variant thereof that is resistant to proteolytic cleavage.

In a related aspect, the present invention provides IGFBP-3 derivatives which are resistant to proteolytic cleavage, which display binding affinities for IGF-I, IGF-II and heparin that are identical or substantially similar to the respective binding affinities of wild-type IGFBP-3, but which do not bind ALS. More specifically, such a IGFBP-3 derivative is as defined herein except that amino acid residues 43 to 47 in SEQ ID NO: 3 are replaced with AGGSG (SEQ ID NO: 5) or any variant thereof that does not bind ALS.

In another related aspect, the present invention provides IGFBP-3 derivatives which have an increased affinity for IGFs and an extended plasma half-life. More specifically, such an IGFBP-3 derivative is as defined herein and further comprises, fused thereto, the amino acid sequence of immunoglobulin IgG1 Fc fragment.

In another related aspect, the present invention provides IGFBP-3 derivatives further comprising the amino acid sequence of IGF-I. More specifically, in such an IGFBP-3 derivative the IGF-I is complexed to the IGFBP-3 polypeptidic derivative. In certain preferred embodiments, the amino acid sequence of IGF-I is the amino acid sequence of human IGF-I.

In yet another related aspect, the present invention provides IGFBP-3 derivatives that are amenable to biotinylation by the BirA enzyme. More specifically, such an IGFBP-3 derivative is as defined herein and further comprises a BirA enzyme substrate covalently bound to the terminal end of the C-terminal domain of the IGFBP-3 polypeptide derivative. In certain embodiments, the BirA enzyme substrate has the sequence set forth in SEQ ID NO: 6. In certain embodiments, the IGFBP-3 derivative comprises further biotin covalently bound to the BirA enzyme substrate.

In still another related aspect, the present invention provides IGFBP-3 derivatives which are stable reporter proteins endowed with high affinity for both IGF-I and IGF-II. More specifically, such an IGFBP-3 derivative is as defined herein and further comprises, fused thereto, the amino acid sequence of SeAP (secreted alkaline phosphatase).

The IGFBP-3 polypeptide derivatives of the present invention can be useful in a variety of therapeutic treatments. Thus, in certain embodiments, the IGFBP-3 derivatives described herein, except for those associated with the amino acid sequence of IGF-1, are provided for use in the treatment of a disorder selected from cancers and vasculo proliferative retinopathies. In other embodiments, the IGFBP-3 derivatives associated with the amino acid sequence of IGF-I are provided for use in the treatment of a disorder selected from the group consisting of growth hormone resistance, IGF-I deficiency, severe burns, HIV wasting, cystic fibrosis, celiac disease, anorexia nervosa, muscle wasting disease, myotonic dystrophy, amyotrophic lateral sclerosis, osteoporosis, severe insulin resistance, type I diabetes, type II diabetes, brain ischemia, heart ischemia, and grafts.

In a related aspect, the present invention provides a method of treatment of a disorder in a subject, the method comprising a step of administering an effective amount of an inventive IGFBP-3 derivative to the subject. Administration of an inventive IGFBP-3 derivative to a subject may be by any suitable route, including for example, parenteral, aerosol, oral, intraocular and topical routes. The inventive IGFBP-3 derivative may be administered alone or in combination with any additional therapeutic agent or procedure. In certain embodiments, the disorder to be treated is selected from the group consisting of cancers and proliferative retinopathies. In other embodiments, the disorder to be treated is selected from the group consisting of growth hormone resistance, IGF-I deficiency, severe burns, HIV wasting, cystic fibrosis, celiac disease, anorexia nervosa, muscle wasting disease, myotonic dystrophy, amyotrophic lateral sclerosis, osteoporosis, severe insulin resistance, type I diabetes, type II diabetes, brain ischemia, neurodegenerative conditions (such as Alzheimer's disease), heart ischemia, retinopathy of prematurity, and grafts.

The inventive IGFBP-3 derivatives may be administered per se or as pharmaceutical compositions. Accordingly, in another aspect, the present invention provides for the use of an inventive IGFBP-3 derivative for the manufacture of medicaments, pharmaceutical compositions or pharmaceutical kits for the treatment of a disorder selected from the group consisting of cancers and proliferative retinopathies or for the treatment of a disorder selected from the group consisting of growth hormone resistance, IGF-I deficiency, severe burns, HIV wasting, cystic fibrosis, celiac disease, anorexia nervosa, muscle wasting disease, myotonic dystrophy, amyotrophic lateral sclerosis, osteoporosis, severe insulin resistance, type I diabetes, type II diabetes, brain ischemia, heart ischemia, and grafts.

In a related aspect, the present invention provides a pharmaceutical composition comprising an effective amount of an inventive IGFBP-3 derivative and at least one physiologically acceptable carrier or excipient. In certain embodiments, the pharmaceutical composition is adapted for administration in combination with at least one additional therapeutic agent. In other embodiments, the pharmaceutical composition further comprises at least one additional therapeutic agent.

In another aspect, the present invention provides a method for determining pro-IGF-II concentration in a biological sample, the method comprising steps of:

contacting the biological sample with an IGFBP-3 polypeptide derivative comprising, fused thereto, the amino acid sequence of SeAP, so as to allow formation of a complex between the IGFBP-3 derivative and any pro-IGF-II present in the biological sample, wherein pro-IGF-II is a partially processed form of IGF-II; and determining the concentration of pro-IGF-II in the biological sample by measuring the alkaline activity of SeAP in the complex In related aspect, the present invention provides a kit comprising an IGFBP-3 polypeptide derivative comprising, fused thereto, the amino acid sequence of SeAP and at least one reagent to measure alkaline activity.

These and other objects, advantages and features of the present invention will become apparent to those of ordinary skill in the art having read the following detailed description of the preferred embodiments.

DEFINITIONS

Figure 1:
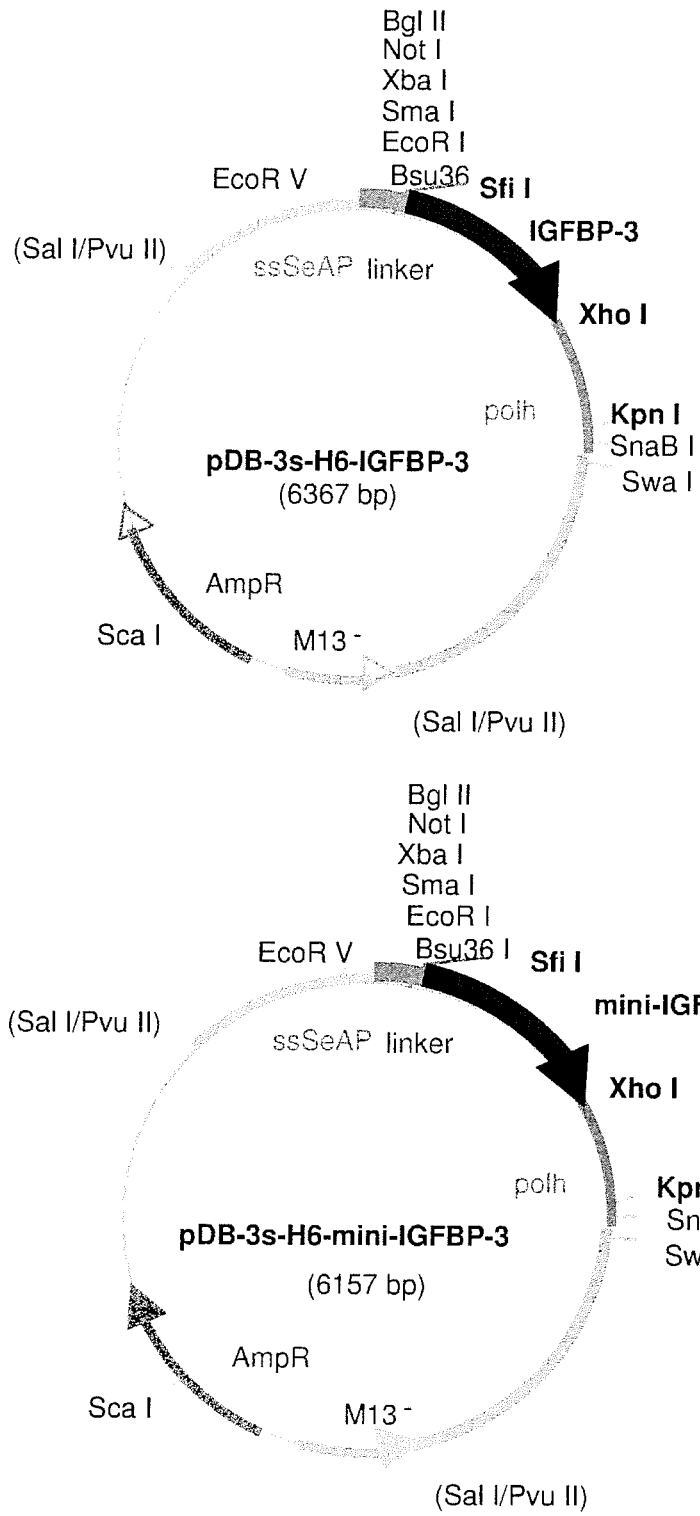
FIG. 1 shows a restriction map of the pDB3s-H6-IGFBP-3 plasmid (top panel) subsequently used as a template to generate, by site-directed mutagenesis the mutant plasmid (pDB3s-H6-IGFBP-3) encoding H6-mini-IGFBP-3 (lower panel). The latter plasmid encodes the mini-IGFBD-3 protein outlined in FIG. 2.

Throughout the specification, several terms are employed that are defined in the following paragraphs.

As used herein, the term "subject" refers to a human or another mammal (e.g., primate, mouse, rat, rabbit, and the like). In many embodiments of the present invention, the subject is a human being. In such embodiments, the subject is often referred to as an "individual" or a "patient". The terms "individual" and "patient" do not denote a particular age.

The term "treatment" is used herein to characterize a method or process that is aimed at (1) delaying or preventing the onset of a disease or condition; (2) slowing down or stopping the progression, aggravation, or deterioration of the symptoms of the disease or condition; (3) bringing about amelioration of the symptoms of the disease or condition; or (4) curing the disease or condition. A treatment may be administered prior to the onset of the disease or condition, for a prophylactic or preventive action. Alternatively or additionally, a treatment may be administered after initiation of the disease or condition, for a therapeutic action.

A "pharmaceutical composition" is defined herein as comprising an effective amount of at least one IGFBP-3 polypeptide derivative of the invention, and at least one pharmaceutically acceptable carrier or excipient.

As used herein, the term "effective amount" refers to any amount of a compound, agent, antibody, or composition that is sufficient to fulfil its intended purpose(s), e.g., a desired biological or medicinal response in a cell, tissue, system or subject.

The term "pharmaceutically acceptable carrier or excipient" refers to a carrier medium which does not interfere with the effectiveness of the biological activity of the active ingredient(s) and which is not excessively toxic to the host at the concentration at which it is administered. The term includes solvents, dispersion, media, coatings, antibacterial and antifungal agents, isotonic agents, and adsorption delaying agents, and the like. The use of such media and agents for pharmaceutically active substances is well known in the art (see for example "Remington's Pharmaceutical Sciences", E. W. Martin, $18^{th}$ Ed., 1990, Mack Publishing Co.: Easton, Pa., which is incorporated herein by reference in its entirety).

The term "isolated", as used herein in reference to a protein or polypeptide, means a protein or polypeptide, which by virtue of its origin or manipulation is separated from at least some of the components with which it is naturally associated or with which it is associated when initially obtained. By "isolated", it is alternatively or additionally meant that the protein or polypeptide of interest is produced or synthesized by the hand of man.

The terms "protein", "polypeptide", and "peptide" are used herein interchangeably, and refer to amino acid sequences of a variety of lengths, either in their neutral (uncharged) forms or as salts, and either unmodified or modified by glycosylation, side-chain oxidation, or phosphorylation. In certain embodiments, the amino acid sequence is a full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversions of the chains such as oxidation of sulfydryl groups. Thus, the term "protein" (or its equivalent terms) is intended to include the amino acid sequence of the full-length native protein, or a fragment thereof, subject to those modifications that do not significantly change its specific properties. In particular, the term "protein" encompasses protein isofoinis, i.e., variants that are encoded by the same gene, but that differ in their pI or MW, or both. Such isoforms can differ in their amino acid sequence (e.g., as a result of allelic variation, alternative splicing or limited proteolysis), or in the alternative, may arise from differential post-translational modification (e.g., glycosylation, acylation, phosphorylation).

The term "analog", as used herein in reference to a protein or protein portion, refers to a polypeptide that possesses a function similar or identical to that of the protein or protein portion but need not necessarily comprise an amino acid sequence that is similar or identical to the amino acid sequence of the protein or protein portion or a structure that is similar or identical to that of the protein or protein portion. Preferably, in the context of the present invention, a protein analog has an amino acid sequence that is at least 30%, more preferably, at least 35%, 40%, 45%, 50%, 55%, 60%, 65%, 70%, 75%, 80%, 85%, 90%, 95% or 99% identical to the amino acid sequence of the protein or protein portion.

The term "protein fragment" refers to a polypeptide comprising an amino acid sequence of at least 5 consecutive amino acid residues (preferably, at least about: 10, 15, 20, 25, 30, 35, 40, 50, 60, 70, 80, 90, 100, 125, 150, 175, 200, 250 or more amino acid residues) of the amino acid sequence of a protein. The fragment of a protein may or may not possess a functional activity of the protein.

The term "biologically active", as used herein to characterize a variant, analog or fragment of a protein or protein portion, refers to a molecule that shares sufficient amino acid sequence identity or homology with the protein or protein portion to exhibit similar or identical properties to the protein or protein portion. For example, in many embodiments of the present invention, a biologically active fragment of the N-terminal domain of IGFBP-3 is a fragment that retains the ability of the N-terminal domain of IGFBP-3 to bind IGF-I, IGF-II, heparin and ALS. Similarly, a biologically active fragment of the C-terminal domain of IGFBP-3 is a fragment that retains the ability of the C-terminal domain of IGFBP-3 to bind IGF-I, IGF-II, heparin and ALS.

The term "homologous" (or "homology"), as used herein, is synonymous with the term "identity" and refers to the sequence similarity between two polypeptide molecules or between two nucleic acid molecules. When a position in both compared sequences is occupied by the same base or same amino acid residue, the respective molecules are then homologous at that position. The percentage of homology between two sequences corresponds to the number of matching or homologous positions shared by the two sequences divided by the number of positions compared and multiplied by 100. Generally, a comparison is made when two sequences are aligned to give maximum homology. Homologous amino acid sequences share identical or similar amino acid sequences. Similar residues are conservative substitutions for, or "allowed point mutations" of, corresponding amino acid residues in a reference sequence. "Conservative substitutions" of a residue in a reference sequence are substitutions that are physically or functionally similar to the corresponding reference residue, e.g. that have a similar size, shape, electric charge, chemical properties, including the ability to from covalent or hydrogen bonds, or the like. Particularly preferred conservative substitutions are those fulfilling the criteria defined for an "accepted point mutation" as described by Dayhoff et al. ("Atlas of Protein Sequence and Structure", 1978, Nat. Biomed. Res. Foundation, Washington, D.C., Suppl. 3, 22: 354-352).

The terms "approximately" and "about", as used herein in reference to a number, generally include numbers that fall within a range of 10% in either direction of the number (greater than or less than the number) unless otherwise stated or otherwise evident from the context (except where such number would exceed 100% of a possible value).

DETAILED DESCRIPTION OF CERTAIN PREFERRED EMBODIMENTS

As mentioned above, the present invention provides IGFBP-3 polypeptide derivatives that are resistant to proteolytic cleavage. These IGFBP-3 derivatives can find application in a wide variety of therapeutic and/or diagnostic applications.

I—IGFBP-3 Polypeptide Derivatives

An IGFBP-3 polypeptide derivative according to the present invention generally comprises an N-terminal domain, an intermediary domain and a C-terminal domain, wherein: (a) the N-terminal domain comprises, or alternatively consists of, the amino acid sequence of the N-terminal domain of wild-type IGFBP-3, of a biologically active variant thereof or of a biologically active fragment thereof; (b) the intermediary domain comprises a linker resistant to proteolytic cleavage; and (c) the C-terminal domain comprises, or alternatively consists of, the amino acid sequence of the C-terminal domain of wild-type IGFBP-3, of a biologically active variant thereof or of a biologically active fragment thereof.

The term "wild-type", as used herein to characterize IGFBP-3 or an IGFBP-3 portion, has its art understood meaning and refers to the naturally-occurring (or native) sequence of IGFBP-3 or IGFBP-3 portion. In certain preferred embodiments of the present invention, wild-type IGFBP-3 is wild-type human IGFBP-3.

Human IGFBP-3

As mentioned above, the IGFs are present throughout the human body almost entirely in association with six specific, high-affinity binding proteins (IGFBP-1 to 6), which are critical determinants of IGF availability and actions. More than 90% of the plasma IGF-1 is bound to IGFBP-3, the most abundant of the six IGFBPs identified. In addition to acting as the main circulating carrier protein, IGFBP-3 is produced in many tissues where it has multiple effects on cell functions both via its ability to modulate IGF actions and also due to direct intrinsic actions.

In humans, IGFBP-3 is encoded by the IGFBP3 gene. Alternative transcriptional variants encoding different isoforms, have been characterized. Two alternative transcripts are known under Accession Number NP_000589.2 and NP_001013416.1.

Thus, in certain embodiments, the N-terminal domain of an IGFBP-3 derivative according to the invention comprises, or alternatively consists of, the amino acid sequence of the N-terminal domain of wild-type human IGFBP-3, i.e., the amino acid sequence of the N-terminal domain of any IGFBP-3 naturally occurring in humans. In other embodiments, the N-terminal domain of a IGFBP-3 derivative according to the invention comprises, or alternatively consists of, the amino acid sequence of a biologically active fragment of the N-terminal domain of wild-type human IGFBP-3, i.e., the amino acid sequence of a fragment of the N-terminal domain of wild-type human IGFBP-3 that retains the ability of the N-terminal domain of wild-type human IGFBP-3 to bind IGF-I, IGF-II, heparin and ALS (Acid Labile Subunit). In yet other embodiments, the N-terminal domain of a IGFBP-3 derivative according to the invention comprises, or alternatively consists of, the amino acid sequence of a biologically active variant of the N-terminal domain of wild-type human IGFBP-3, i.e., the amino acid sequence of a polypeptide that differs from the wild-type human IGFBP-3 by deletions, substitutions, additions and/or alterations but whose overall sequence similarity to the wild-type human IGFBP-3 is such that it exhibits at least an identical or a similar, if not a higher, binding affinity for IGF-I, IGF-II, heparin and ALS than the N-terminal domain of wild-type human IGFBP-3. In certain preferred embodiments, the amino acid sequence of the N-terminal domain of wild-type human IGFBP-3 is as set forth in SEQ ID NO: 1.

Similarly, in certain embodiments, the C-terminal domain of an IGFBP-3 derivative according to the invention comprises, or alternatively consists of, the amino acid sequence of the C-terminal domain of wild-type human IGFBP-3, i.e., the amino acid sequence of the C-terminal domain of any IGFBP-3 naturally occurring in humans. In other embodiments, the C-terminal domain of a IGFBP-3 derivative according to the invention comprises, or alternatively consists of, the amino acid sequence of a biologically active fragment of the C-terminal domain of wild-type human IGFBP-3, i.e., the amino acid sequence of a fragment of the C-terminal domain of wild-type human IGFBP-3 that retains the ability of the C-terminal domain of wild-type human IGFBP-3 to bind IGF-I, IGF-II, heparin and ALS. In yet other embodiments, the C-terminal of a IGFBP-3 derivative according to the invention comprises, or alternatively consists of, the amino acid sequence of a biologically active variant of the C-terminal domain of wild-type human IGFBP-3, i.e., the amino acid sequence of a polypeptide that differs from the wild-type human IGFBP-3 by deletions, substitutions, additions and/or alterations but whose overall sequence similarity to the wild-type human IGFBP-3 is such that it exhibits at least an identical or a similar, if not a higher, binding affinity for IGF-I, IGF-II, heparin and ALS than wild-type human IGFBP-3. In certain preferred embodiments, the amino acid sequence of the C-terminal domain of wild-type human IGFBP-3 is as set forth in SEQ ID NO: 3.

Linker Resistant to Proteolytic Cleavage

The IGFBP-3 derivatives of the present invention are characterized by a resistance to proteolytic cleavage. As mentioned above, the intermediate domain of wild-type IGFBP-3 is loosely structured and is the target of proteolytic cleavage. Several proteases have been shown to cleave IGFBP-3 including plasmin, thrombin, kallikrein, prostate-specific antigen, matrix metalloproteases, and cathepsin. Proteolysis of IGFBP-3 lowers its affinity for IGF, thus increasing the overall ratio of free IGF to total bound IGF.

In contrast, the IGFBP-3 derivatives according to the invention were designed to be resistant to proteolytic cleavage. The term "resistant to proteolytic cleavage", when used herein in reference to an IGFBP-3 derivative (or to a linker) means that the IGFBP-3 derivative (or the linker) does not undergo significant (i.e., detectable) enzymatic degradation in vitro and/or in vivo when in the presence of proteases that cleave wild-type IGFBP-3. One skilled in the art would know how to test and assess the susceptibility of a polypeptide to proteolytic cleavage.

The resistance to the degrading action of proteases exhibited by an IGFBP-3 derivative of the present invention results from the fact its intermediary domain is designed to be resistant to proteolytic cleavage. In certain embodiments, the intermediary domain consists of a linker that is resistant to proteolytic cleavage. In other embodiments, the intermediary domain comprises a linker that is resistant to proteolytic cleavage. For example, the intermediary domain of an IGFBP-3 derivative of the present invention may comprise, or alternatively may consist of, the amino acid sequence of the intermediary domain of wild-type IGFBP-3, wherein a portion of said amino acid sequence is replaced with a linker resistant to proteolytic cleavage. In embodiments where wild-type IGFBP-3 is wild-type human IGFBP-3, the amino acid sequence of the intermediary domain of wild-type IGFBP-3 may be as set forth in SEQ ID NO: 2.

In general, the portion of the amino acid sequence of the intermediary domain of wild-type IGFBP-3 that is replaced with a linker resistant to proteolytic cleavage is such that the resulting intermediary domain of the IGFBP-3 derivative is resistant to proteolytic cleavage. Thus, preferably, the portion of the amino acid sequence of the intermediary domain of wild-type IGFBP-3 that is replaced with a linker resistant to proteolytic cleavage is a substantial portion of the amino acid sequence of the intermediary domain of wild-type IGFBP-3. As used herein, the term "substantial portion of the amino acid sequence of the intermediary domain of wild-type IGFBP-3" refers to at least 85% of the entire intermediary domain of wild-type IGFBP-3, or at least 87%, at least 88%, at least 89%, at least 90% or more than 90% of the entire intermediary domain of wild-type IGFBP-3. Alternatively or additionally, the term "substantial portion of the amino acid sequence of the intermediary domain of wild-type IGFBP-3" refers to 85 contiguous amino acid residues of the intermediary domain of IGFBP-3 or more than 85 contiguous amino acid residues of the intermediary domain of IGFBP-3, such as for example, 86, 87, 88, 89, 90, 91 or 92 contiguous amino acid residues of the intermediary domain of IGFBP-3.

In the context of the present invention, the linker resistant to proteolytic cleavage may be any polypeptide that does not undergo any significant enzymatic degradation in vitro and/or in vivo when in the presence of proteases that cleave wild-type IGFBP-3. In certain preferred embodiments, the linker has the sequence set forth in SEQ ID NO: 4 or the sequence of any variant of SEQ ID NO: 4 that is resistant to proteolytic cleavage.

In certain embodiments, the linker may comprise an element of conditional proteolysis, i.e. an entity that undergoes proteolysis only under specific conditions. Strategies and systems to render a protein or a polypeptide subject to conditional proteolysis are known in the art.

Mini IGFBP-3 Derivatives

The IGFBP-3 derivatives, as described above, share at least two main properties: (1) they are resistant to proteolytic cleavage, and (2) they display binding affinities for IGF-I, IGF-II, heparin and ALS that are identical to, substantially similar or even higher than the corresponding binding affinities of wild-type IGFBP-3. The present inventors have called these IGFBP-3 derivatives, "mini-IGFBP-3".

Using mini-IGFBP-3 as a platform or cornerstone of their project, the inventors have designed and developed other IGFBP-3 derivatives with different properties and potential applications.

Mini-IGFBP-3 ALS− Derivatives

Thus, in one aspect, the present invention provides IGFBP-3 derivatives that (1) are resistant to proteolytic cleavage, (2) display binding affinities for IGF-I, IGF-II and heparin that are identical, substantially similar or even higher than the corresponding binding affinities of wild-type IGFBP-3, but (3) that do not (or do not substantially) bind to ALS. These IGFBP-3 derivatives are herein termed "mini-IGFBP-3 ALS−" derivatives.

Such a mini-IGFBP-3 ALS− derivative generally comprises an N-terminal domain, an intermediary domain and a C-terminal domain, wherein: (a) the N-terminal domain comprises, or alternatively consists of, the amino acid sequence of the N-terminal domain of wild-type IGFBP-3, of a biologically active variant thereof or of a biologically active fragment thereof; (b) the intermediary domain comprises a linker resistant to proteolytic cleavage; and (c) the C-terminal domain comprises, or alternatively consists of, the amino acid sequence of the C-terminal domain of wild-type IGFBP-3, of a biologically active variant thereof or of a biologically active fragment thereof, wherein the portion of the C-terminal domain that binds to ALS is replaced with AGGSG (SEQ ID NO: 5) or any variant of SEQ ID NO: 5 that does not bind ALS.

In embodiments where wild-type IGFBP-3 is wild-type human IGFBP-3 and the amino acid sequence of the C-terminal domain of wild-type human IGFBP-3 is as set forth in SEQ ID NO: 3, amino acid residues 43 to 47 in SEQ ID NO: 3 are replaced with AGGSG (SEQ ID NO: 5) or any variant thereof that does not bind ALS.

Mini-IGFBP-3-Fc Derivatives

The present invention also provides IGFBP-3 derivatives that (1) are resistant to proteolytic cleavage, (2) display binding affinities for IGF-I and/or IGF-II that are higher than the corresponding affinities of wild-type IGFBP-3, and (3) have a plasma half-life that is longer than the plasma half-live of wild-type IGFBP and/or of other mini-IGFBP-3 derivatives. These IGFBP-3 derivatives are termed "mini-IGFBP-3-Fc" derivatives.

Indeed, a mini-IGFBP-3-Fc derivative of present invention comprises the immunoglobulin IgG1 Fc fragment fused thereto, in addition to an N-terminal domain, an intermediary domain and a C-terminal domain as defined herein. The term "immunoglobulin IgG1 Fc fragment" has herein its art understood meaning and refers to the fragment crystallizable region of an antibody of the IgG1 class of globulin proteins that are the most abundant in human serum. Preferably, the immunoglobulin IgG1 Fc fragment is fused to the terminal end of the C-terminal domain of the IGFBP-3-Fc derivative. In certain embodiments, each "arm" of the IgG1 Fc fragment (i.e., each of the two identical polypeptides constituting the Fc fragment) is fused to the terminal end of the C-terminal domain of a mini-IGFBP-3 derivative. Consequently, the present invention also provides a fusion protein comprising the immunoglobulin IgG1 Fc fragment fused to two mini-IGFBP-3-Fc derivatives. The inventors have found that such a fusion protein (see Examples section) has an apparent affinity $IC_{50}$ that is sevenfold higher than that of IGFBP-3 derivatives that are not fused to IgG1 Fc fragment.

As will be understood by one skilled in the art, the mini-IGFBP-3 part of a "mini-IGFBP-3-Fc" fusion protein may or may not be modified to exhibit no (or insignificant) binding to ALS, as described above.

Mini-IGFBP-3/IGF-I Complexes

The present invention also provides IGFBP-3/IGF-I complexes that are resistant to proteolytic cleavage.

Such a IGFBP-3/IGF-I complex generally comprises an N-terminal domain, an intermediary domain and a C-terminal domain, as defined herein, and further comprises the amino acid sequence of IGF-I, wherein IGF-I is complexed to the IGFBP-3 polypeptide derivative. As used herein, the term "IGF-I" has its art understood meaning and refers to a small protein (~7,500 kDa) called insulin-like growth factor 1 that, in humans, is encoded by the IGF1 gene (Accession Numbers NP_0011004753, NP_001104754, and NP_000609).

IGF-I consists of single chain of amino acids with three intramolecular disulfide bridges. It is originally synthesized as a biologically inactive pro-IGF-I peptide, which subsequently undergoes regulated endoproteolytic cleavage to the mature form. In the context of the present invention, the amino sequence of IGF-I preferably comprises (or alternatively consists of) the amino acid sequence of wild-type human IGF-I (i.e., of any IGF-I naturally occurring in humans), or a biologically active fragment thereof or a biologically active variant thereof. Suitable biologically active fragments and variants of wild-type human IGF-I encompass those fragments and variants that retain the biological properties of wild-type human IGF-I (in particular binding to IGFBP-3 and to IGF-1R).

In an IGFBP-3/IGF-I complex, the IGFBP-3 derivative and the IGF-I are associated by non-covalent bounds. Non-covalent interactions include hydrogen bonds, ionic bonds, van der Waals forces, and hydrophobic interactions. In general, in an IGFBP-3/IGF-I complex, the IGFBP-3 derivative and the IGF-I are associated in a manner that is identical or similar to that of a naturally occurring IGFBP-3/IGF-I complex (within the body).

In certain embodiments, the linker of a mini-IGFBP-3:IGF-I complex of the present invention comprises an element of conditional proteolysis, as defined above. For example, the element of conditional proteolysis may be designed to allow the targeted delivery of IGF-I.

Mini-IGFBP-3-Avitag Derivatives

The present invention also provides IGFBP-3 derivatives that (1) are resistant to proteolytic cleavage, (2) display binding affinities for IGF-I, IGF-II, heparin and ALS that are identical to, substantially similar or even higher than the corresponding binding affinities of wild-type IGFBP-3, and (3) that are amenable to biotinylation by the BirA enzyme. These IGFBP-3 derivatives are termed "mini-IGFBP-3-avitag" derivatives.

Such a mini-IGFBP-3-avitag derivative generally comprises an N-terminal domain, an intermediary domain and a C-terminal domain, as defined herein, and further comprises a BirA enzyme substrate covalently bound to the terminal end of the C-terminal domain of the IGFBP-3 derivative. As used herein "BirA enzyme" has its art understood meaning and refers to the E. Coli biotin ligase enzyme that has the ability to biotinylate proteins at a specific residue in a recognition sequence (or BirA enzyme substrate) (O'callaghan et al., Anal. Biochem., 1999, 266: 9-15). As used herein, the term "BirA enzyme substrate" refers to and encompasses any target amino acid sequence that is recognized by the BirA enzyme and to which the BirA enzyme can attach a biotin. A variety of BirA enzyme substrates are known in the art, including those described for example in U.S. Pat. No. 5,723,584, U.S. Pat. No. 5,487,993, EP 0 550 693 and WO 95/04069, which are suitable for use in the context of the present invention. However, in certain preferred embodiments, the BirA enzyme substrate has the sequence set forth in SEQ ID NO: 6.

The present invention further provides a mini-IGFBP-3-avitag derivative generally comprising an N-terminal domain, an intermediary domain and a C-terminal domain, as defined herein, and further comprising a BirA enzyme substrate covalently linked to the terminal end of the C-terminal domain of the IGFBP-3 derivative and a biotin molecule covalently attached to the BirA enzyme substrate. These IGFBP-3 derivatives are herein termed "mini-IGFBP-3-avitag-biotin" derivatives.

As will be understood by one skilled in the art, the mini-IGFBP-3 part of a mini-IGFBP-3-avitag derivative or of a mini-IGFBP-3-avitag-biotin derivative may or may not be modified to exhibit no (or insignificant) binding to ALS, as described above.

SeAP-Mini-IGFBP-3 Derivatives

The present invention also provides IGFBP-3 derivatives that (1) are resistant to proteolytic cleavage, (2) display binding affinities for IGF-I, IGF-II, heparin and ALS that are identical to, substantially similar or even higher than the corresponding binding affinities of wild-type IGFBP-3, and (3) that are detectable by being labeled with a reporter protein. For example, the reporter protein may be luciferase, β-galactosidase, alkaline phosphatase, and the like. When the reporter protein is alkaline phosphatase, these IGFBP-3 derivatives are termed "SeAP-mini-IGFBP-3" derivatives.

Such a SeAP-mini-IGFBP-3 derivative generally comprises an N-terminal domain, an intermediary domain, and a C-terminal domain, as defined herein and further comprises, fused to the terminal end of the N-terminal domain, the amino acid sequence of SeAP (secreted alkaline phosphatase). As will be understood by one skilled in the art, the mini-IGFBP-3 part of a SeAP-mini-IGFBP-3 derivative may or may not be modified to exhibit no (or insignificant) binding to ALS, as described above.

The terms "SeAP" and "secreted alkaline phosphatase" are used herein interchangeably. They refer to an enzyme, encoded by the SEAP gene (GenBank Accession Number NP_001623), and that is a truncated form of human placental alkaline phosphatase (PLAP). SEAP has the unusual properties of being extremely heat-stable and resistant to the phosphatase inhibitor L-homoarginine (Micanovic et al., Proc. Natl. Acad. Sci., USA, 1990, 87: 157-161).

Preparation of the IGFBP-3 Derivatives

The IGFBP-3 derivatives according to the present invention may be prepared using any of a variety of suitable methods known in the art, including site-directed mutagenesis and recombinant techniques such as those employed by the present inventors (see Examples section). The invention encompasses the expression vectors developed by the present inventors as well as host cells comprising such expression vectors.

II—Uses of IGFBP-3 Polypeptide Derivatives

The IGFBP-3 polypeptide derivatives of the present invention may be used in a variety of therapeutic and/or diagnostic applications. They have the advantage of being derived from a protein of human origin, which is already approved by the FDA for some therapeutic indications and which has proved to be associated with no major secondary effects.

1—Therapeutic Applications

A. Indications

The IGFBP-3 polypeptide derivatives of the present invention may be useful as agents that sequester IGFs (IGF-I and/or IGF-II) and thereby reduce their bioavailability. As such they may constitute an alternative to existing anti- IGF1-R monoclonal antibodies and tyrosine kinase inhibitors as adjuvants in the chemotherapy or radiotherapy of human malignancies (Klinakis et al., Proc. Natl. Acad. Sci. USA, 2009, 106: 2359-2364; Pollack et al., Nat. Rev. Cancer, 2004, 4: 505-518; Ryan and Goss; Oncologist, 2008, 13: 16-24; Sachdev and Yee, Mol. Cancer Ther., 2007, 6: 1-12; Samani et al., Endocr. Rev. 2006). Some IGFBP-3 polypeptide derivatives of the present invention, such as mini-IGFBP-3-Fc, are able to sequester both IGF-I and IGF-II present in the bloodstream, whereas others, such as mini-IGFBP-3 ALS⁻ are able to reduce bioavailable tissue IGFs. This latter feature could be further targeted to the tumor tissue itself by appending a biotin residue to the IGFBP-3 derivative (mini-IGFBP-3-ALS-avitag-biotin). In both strategies, administration of an IGFBP-3 polypeptide derivative of the present invention results in the down regulation of the IGF signaling pathway. This approach seems particularly relevant and promising in the case of metastatic tumor patients, where the circulation of intact IGFBP-3 is strongly depressed (Fowlkes et al., Endocr., 2004, 145: 620-626; Miyamoto et al., Cancer Res., 2004, 64: 665-371; Nakamura et al., Biochem. Biophys. Res. Commun., 2005, 333: 1011-1016). The administration of protease-resistant IGFBP-3 polypeptide derivatives will produce a sustained IGF deprivation deleterious to the tumor that should potentiate the effects of other chemotherapeutic agents to reduce tumor load.

IGFs sequestration by an IGFBP-3 polypeptide derivative of the present invention can also be beneficial in the management of certain ophthalmic disorders. Examples of ophthalmic disorders associated with an IGF-I excess that can be treated according to the present invention include, but are not limited to, proliferative retinopathies, such as Age Related Macular Degeneration and diabetic retinopathy in which IGF-I has been shown to be responsible for pathogenic VEGF overproduction (Chang et al., Proc. Natl. Acad. Sci. USA, 2007, 104: 10595-10600; Grant et al., Expert Opin. Invest. Drugs, 2004, 13: 1275-1293). Other examples include retinal wounds, secondary cataracts, corneal epithelial wounds and Sjogren's syndrome. In such applications, an IGFBP-3 polypeptide derivative of the present invention may be administered, for example, by intraocular injection or by application to the cornea (e.g., via eyedrops or a timed release capsule placed in the cul de sac).

An IGFBP-3 derivative of the present invention may also be used as a vector to supply IGF-1 when systematic administration of IGF-1 is indicated. Such indications include, but are not limited to growth hormone resistance, IGF-I deficiency, severe burns, HIV wasting, cystic fibrosis, celiac disease, anorexia nervosa, muscle wasting disease, myotonic dystrophy, amyotrophic lateral sclerosis, osteoporosis, severe insulin resistance (Clemmons, Nat. Rev. Drug Discov., 2007, 6: 821-833), type I diabetes, type II diabetes, brain ischemia, heart ischemia, and grafts.

Methods of treatment of the present invention may be accomplished using an inventive IGFBP-3 polypeptide derivative or a pharmaceutical composition thereof. These methods generally comprise administration of an effective amount of at least one IGFBP-3 polypeptide derivative (as defined above), or a pharmaceutical composition thereof, to a subject in need thereof. Administration may be performed using any of the methods known to one skilled in the art. In particular, an IGFBP-3 polypeptide derivative or composition thereof may be administered by any of various routes including, but not limited to, aerosol, parenteral, oral or topical route.

In general, an inventive IGFBP-3 derivative or a composition thereof will be administered in an effective amount, i.e., an amount that is sufficient to fulfill its intended purpose. The exact amount of IGFBP-3 derivative or pharmaceutical composition to be administered will vary from subject to subject, depending on the age, sex, weight and general health condition of the subject to be treated, the desired biological or medical response and the like. In certain embodiments, an effective amount is one that allows efficient down regulation of the IGF signaling pathway, efficient sequestration of IGF-I and/or IGF-II present in the bloodstream, and/or efficient reduction of bioavailable tissue IGF. In other embodiments, an effective amount is one that allows efficient supply of IGF-1. In most embodiments, an effective amount of an IGFBP-3 derivative or of a pharmaceutical composition thereof is one that results in treatment of the disorder for which it is administered, e.g. slowing down or stopping the progression, aggravation or deterioration of the symptoms of the disorder and/or bringing about amelioration of the symptoms of the disorder, and/or curing the disorder. The effects of a treatment according to the invention may be monitored using any of the assays known in the art for the diagnosis of the disease being treated.

In certain embodiments, an IGFBP-3 polypeptide derivative or a composition thereof is administered alone according to a method of treatment of the present invention. In other embodiments, an IGFBP-3 polypeptide derivative or a composition thereof is administered in combination with at least one additional therapeutic agent or therapeutic procedure. The IGFBP-3 polypeptide derivative or composition may be administered prior to administration of the therapeutic agent or therapeutic procedure, concurrently with the therapeutic agent or procedure, and/or following administration of the therapeutic agent or procedure.

Therapeutic agents that may be administered in combination with an inventive IGFBP-3 polypeptide derivative or composition may be selected among a large variety of biologically active compounds that are known to have a beneficial effect in the treatment of the disease for which the IGFBP-3 derivative is administered (e.g. anti-cancer agents, anti-inflammatory agents, immunomodulatory agents, analgesics, antimicrobial agents, antibacterial agents, antibiotics, antioxidants, antiseptic agents, and combinations thereof). Therapeutic procedures that may be performed in combination with administration of an inventive IGFBP-3 polypeptide derivative or composition include, but are not limited to, surgery, radiotherapy, and the like.

More specific examples of pathological contexts in which an inventive IGFBP-3 polypeptide derivative or composition can be beneficially administered alone or in association with other therapies include non small cell lung cancer and forms of the disease having developed resistance to EGFR targeted therapies (Gefitinib, Erlotinib), hepatocellular carcinoma (Sorafenib) and forms that have developed resistance to such agent, HER2-amplified breast cancer associated to HER2 targeted therapies (Trastuzumab) and forms that have developed resistance to this agent, Estrogen Receptor positive (ER+) breast cancer in association with hormone therapies and noticeably a subset of Estrogen Receptor positive (ER+) breast cancers with low levels of ER which do not respond to hormonal therapy (luminal B), some triple negative breast cancers, breast cancers developing resistance to Estrogen Receptor-targeted therapies (Fulvestant), gastrointestinal stromal tumors, being either insensitive or resistant to PDGFR targeted therapies (Imatinib), resistance to Androgen Receptor-targeted therapies in prostate cancer, resistance to BRAFV600E targeted therapies of melanoma and colon cancer, therapy of IGF-I-producing Ewing's sarcoma and other sarcomas, therapy multiple myeloma (noticeably of IGF-I-producing myelomas) in association with other therapies, therapy hepatocellular carcinomas (noticeably of IGF-II-producing tumors), therapy of colon adenocarcinoma (noticeably IGF-II-producing tumor), therapy of ovarian cancers (noticeably Epithelial Ovarian Cancer and IGF-II-producing tumors), therapy of adrenocortical carcinoma, therapy of some pancreatic cancers, and as adjuvant of hormonal therapy of breast and prostate cancers, therapy of Squamous Cell Carcinoma of the Head and Neck, therapy of pediatric tumors such as Wilms' tumor, hepatoblastoma, rhabdomyosarcoma, neuroblastoma, but also therapy of adult Glioblastoma, therapy of IGF-II producing tumors such as non islet cell tumor hypoglycemia (NICTH), therapy of osteosarcoma, therapy of mesothelioma.

B. Administration

An IGFBP-3 polypeptide derivative (optionally after formulation with one or more appropriate pharmaceutically acceptable carriers or excipients), in a desired dosage can be administered to a subject in need thereof by any suitable route. Various delivery systems are known and can be used to administer IGFBP-3 derivatives of the present invention, including tablets, capsules, injectable solutions, encapsulation in liposomes, microparticles, microcapsules, etc. Methods of administration include, but are not limited to, dermal, intradermal, intramuscular, intraperitoneal, intralesional, intravenous, subcutaneous, intranasal, pulmonary, epidural, ocular, and oral routes. An inventive IGFBP-3 derivative or composition may be administered by any convenient or other appropriate route, for example, by infusion or bolus injection, by adsorption through epithelial or mucocutaneous linings (e.g., oral, mucosa, rectal and intestinal mucosa, etc). Administration can be systemic or local. Parenteral administration may be directed to a given tissue of the patient, such as by catheterization. As will be appreciated by those of ordinary skill in the art, in embodiments where an inventive IGFBP-3 derivative is administered along with an additional therapeutic agent, the IGFBP-3 derivative and the therapeutic agent may be administered by the same route (e.g., orally) or by different routes (e.g., orally and intravenously).

C. Dosage

Administration of an inventive IGFBP-3 derivative (or a composition thereof) of the present invention will be in a dosage such that the amount delivered is effective for the intended purpose. The route of administration, formulation and dosage administered will depend upon the therapeutic effect desired, the severity of the disorder being treated, the presence of any infection, the age, sex, weight and general health condition of the patient as well as upon the potency, bioavailability and in vivo half-life of the IGFBP-3 derivative used, the use (or not) of concomitant therapies, and other clinical factors. These factors are readily determinable by the attending physician in the course of the therapy. Alternatively or additionally, the dosage to be administered can be determined from studies using animal models. Adjusting the dose to achieve maximal efficacy based on these or other methods are well known in the art and are within the capabilities of trained physicians. As studies are conducted using IGFBP-3 derivatives of the invention, further information will emerge regarding the appropriate dosage levels and duration of treatment.

A treatment according to the present invention may consist of a single dose or multiple doses. Thus, administration of an inventive IGFBP-3 derivative, or composition thereof, may be constant for a certain period of time or periodic and at specific intervals, e.g., hourly, daily, weekly (or at some other multiple day interval); monthly, yearly (e.g., in a time release form). Alternatively, the delivery may occur at multiple times during a given time period, e.g., two or more times per week, two or more times per month, and the like. The delivery may be continuous delivery for a period of time, e.g., intravenous delivery.

2—Diagnostic Applications

Some of the IGFBP-3 polypeptide derivatives of the present invention may be useful in diagnostic applications. In particular, the present invention provides a method for determining pro-IGF-II concentration in a biological sample, the method comprising steps of: (1) contacting the biological sample with an IGFBP-3 polypeptide derivative comprising, fused thereto, the amino acid sequence of SeAP, so as to allow formation of a complex between the IGFBP-3 derivative and any pro-IGF-II present in the biological sample, wherein pro-IGF-II is a partially processed form of IGF-II; and (2) determining the concentration of pro-IGF-II in the biological sample by measuring the alkaline activity of SeAP in the complex.

As used herein, the term "pro-IGF-II" has its art understood meaning and refers to a partially processed form of IGF-II, as it is originally synthesized before undergoing regulated endoproteolytic cleavage to the mature form (IGF-II).

The term "biological sample" is used herein in its broadest sense. A biological sample is generally obtained from a subject. A sample may be of any biological tissue or fluid that may contain pro-IGF-II. In humans, pro-forms of IGF-II have been detected in serum as well as in cerebrospinal and amniotic fluids. Frequently, a biological sample will be a "clinical sample", i.e. a sample derived from a patient, i.e. a subject diagnosed with a disease or suspected of having a disease.

The step of determining the concentration of pro-IGF-II in the biological sample by measuring the alkaline activity of SeAP in the complex may be carried out using any method known in the art, including through the use of p-nitrophenylphosphate as described in the Examples section.

III—Pharmaceutical Compositions

As mentioned above, the IGFBP-3 polypeptide derivatives of the invention may be administered per se or as a pharmaceutical composition. Accordingly, the present invention provides pharmaceutical compositions comprising an effective amount of at least one IGFBP-3 polypeptide derivative and at least one pharmaceutically acceptable carrier or excipient. In some embodiments, the composition further comprises one or more additional biologically active agents.

The IGFBP-3 polypeptide derivatives and pharmaceutical compositions thereof may be administered in any amount and using any route of administration effective for achieving the desired prophylactic and/or therapeutic effect. The optimal pharmaceutical formulation can be varied depending upon the route of administration and desired dosage. Such formulations may influence the physical state, stability, rate of in vivo release, and rate of in vivo clearance of the administered active ingredient.

The pharmaceutical compositions of the present invention may be formulated in dosage unit form for ease of administration and uniformity of dosage. The expression "unit dosage form", as used herein, refers to a physically discrete unit of an IGFBP-3 polypeptide derivative for the patient to be treated. It will be understood, however, that the total daily dosage of the compositions will be decided by the attending physician within the scope of sound medical judgement.

A. Formulation

Injectable preparations, for example, sterile injectable aqueous or oleaginous suspensions may be formulated according to the known art using suitable dispersing or wetting agents, and suspending agents. The sterile injectable preparation may also be a sterile injectable solution, suspension or emulsion in a non-toxic parenterally acceptable diluent or solvent, for example, as a solution in 2,3-butanediol. Among the acceptable vehicles and solvents that may be employed are water, Ringer's solution, U.S.P. and isotonic sodium chloride solution. In addition, sterile, fixed oils are conventionally employed as a solution or suspending medium. For this purpose any bland fixed oil can be employed including synthetic mono- or di-glycerides. Fatty acids such as oleic acid may also be used in the preparation of injectable formulations. Sterile liquid carriers are useful in sterile liquid form compositions for parenteral administration.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Liquid pharmaceutical compositions which are sterile solutions or suspensions can be administered by, for example, intravenous, intramuscular, intraperitoneal or subcutaneous injection. Injection may be via single push or by gradual infusion. Where necessary or desired, the composition may include a local anesthetic to ease pain at the site of injection.

In order to prolong the effect of an active ingredient, it is often desirable to slow the absorption of the ingredient from subcutaneous or intramuscular injection. Delaying absorption of a parenterally administered active ingredient may be accomplished by dissolving or suspending the ingredient in an oil vehicle. Injectable depot forms are made by forming micro-encapsulated matrices of the active ingredient in biodegradable polymers such as polylactide-polyglycolide. Depending upon the ratio of active ingredient to polymer and the nature of the particular polymer employed, the rate of ingredient release can be controlled. Examples of other biodegradable polymers include poly(orthoesters) and poly(anhydrides). Depot injectable formulations can also be prepared by entrapping the active ingredient in liposomes or microemulsions which are compatible with body tissues.

Liquid dosage forms for oral administration include, but are not limited to, pharmaceutically acceptable emulsions, microemulsions, solutions, suspensions, syrups, elixirs, and pressurized compositions. In addition to the IGFBP-3 polypeptide derivative, the liquid dosage form may contain inert diluents commonly used in the art such as, for example, water or other solvent, solubilising agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cotton seed, ground nut, corn, germ, olive, castor, and sesame oils), glycerol, tetrahydrofurfuryl alcohol, polyethylene glycols, and fatty acid esters of sorbitan and mixtures thereof. Besides inert diluents, the oral compositions can also include adjuvants such as wetting agents, suspending agents, preservatives, sweetening, flavouring, and perfuming agents, thickening agents, colors, viscosity regulators, stabilizers or osmo-regulators. Examples of suitable liquid carriers for oral administration include water (potentially containing additives as above, e.g., cellulose derivatives, such as sodium carboxymethyl cellulose solution), alcohols (including monohydric alcohols and polyhydric alcohols such as glycols) and their derivatives, and oils (e.g., fractionated coconut oil and arachis oil). For pressurized compositions, the liquid carrier can be halogenated hydrocarbon or other pharmaceutically acceptable propellant.

Solid dosage forms for oral administration include, for example, capsules, tablets, pills, powders, and granules. In such solid dosage forms, an inventive IGFBP-3 polypeptide derivative may be mixed with at least one inert, pharmaceutically acceptable excipient or carrier such as sodium citrate or dicalcium phosphate and one or more of: (a) fillers or extenders such as starches, lactose, sucrose, glucose, mannital, and silicic acid; (b) binders such as, for example, carboxymethylcellulose, alginates, gelatine, polyvinylpyrrolidone, sucrose, and acacia; (c) humectants such as glycerol; (d) disintegrating agents such as agar-agar, calcium carbonate, potato or tapioca starch, alginic acid, certain silicates, and sodium carbonate; (e) solution retarding agents such as paraffin; absorption accelerators such as quaternary ammonium compounds; (g) wetting agents such as, for example, cetyl alcohol and glycerol monostearate; (h) absorbents such as kaolin and bentonite clay; and (i) lubricants such as talc, calcium stearate, magnesium stearate, solid polyethylene glycols, sodium lauryl sulphate, and mixtures thereof. Other excipients suitable for solid formulations include surface modifying agents such as non-ionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. In the case of capsules, tablets and pills, the dosage form may also comprise buffering agents.

Solid compositions of a similar type may also be employed as fillers in soft and hard-filled gelatine capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. They may optionally contain opacifying agents and can also be of a composition such that they release the active ingredient(s) only, or preferably, in a certain part of the intestinal tract, optionally, in a delaying manner. Examples of embedding compositions which can be used include polymeric substances and waxes.

In certain embodiments, it may be desirable to administer an inventive composition locally to an area in need of treatment. This may be achieved, for example, and not by way of limitation, by local infusion during surgery, topical application, by injection, by means of a catheter, by means of suppository, or by means of a skin patch or stent or other implant.

For topical administration, the composition is preferably formulated as a gel, an ointment, a lotion, or a cream which can include carriers such as water, glycerol, alcohol, propylene glycol, fatty alcohols, triglycerides, fatty acid esters, or mineral oil. Other topical carriers include liquid petroleum, isopropyl palmitate, polyethylene glycol, ethanol (95%), polyoxyethylenemonolaurat (5%) in water, or sodium lauryl sulphate (5%) in water. Other materials such as antioxidants, humectants, viscosity stabilizers, and similar agents may be added as necessary.

In addition, in certain instances, it is expected that the inventive compositions may be disposed within transdermal devices placed upon, in, or under the skin. Such devices include patches, implants, and injections which release the active ingredient by either passive or active release mechanisms. Transdermal administrations include all administration across the surface of the body and the inner linings of bodily passage including epithelial and mucosal tissues. Such administrations may be carried out using the present compositions in lotions, creams, foams, patches, suspensions, solutions, and suppositories (rectal and vaginal).

Transdermal administration may be accomplished through the use of a transdermal patch containing an active ingredient (i.e., the IGFBP-3 polypeptide derivative) and a carrier that is non-toxic to the skin, and allows the delivery of the ingredient for systemic absorption into the bloodstream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may be suitable. A variety of occlusive devices may be used to release the active ingredient into the bloodstream such as a semi-permeable membrane covering a reservoir containing the active ingredient with or without a carrier, or a matrix containing the active ingredient.

Suppository formulations may be made from traditional materials, including cocoa butter, with or without the addition of waxes to alter the suppository's melting point, and glycerine. Water soluble suppository bases, such as polyethylene glycols of various molecular weights, may also be used.

Materials and methods for producing various formulations are known in the art and may be adapted for practicing the subject invention. Suitable formulations for the delivery of antibodies can be found, for example, in "*Remington's Pharmaceutical Sciences*", E. W. Martin, 18$^{th}$ Ed., 1990, Mack Publishing Co.: Easton, Pa.

B. Additional Biologically Active Agents

In certain embodiments, an inventive IGFBP-3 polypeptide derivative is the only active ingredient in a pharmaceutical composition of the present invention. In other embodiments, the pharmaceutical composition further comprises one or more biologically active agents. Examples of suitable biologically active agents include, but are not limited to, anti-cancer agents, anti-inflammatory agents, immunomodulatory agents, analgesics, antimicrobial agents, antibacterial agents, antibiotics, antioxidants, antiseptic agents, and combinations thereof.

In such pharmaceutical compositions, the IGFBP-3 polypeptide derivative and the at least one additional therapeutic agent may be combined in one or more preparations for simultaneous, separate or sequential administration of the IGFBP-3 polypeptide derivative and therapeutic agent(s). More specifically, an inventive composition may be formulated in such a way that the IGFBP-3 polypeptide derivative and therapeutic agent(s) can be administered together or independently from each other. For example, an IGFBP-3 polypeptide derivative and a therapeutic agent can be formulated together in a single composition. Alternatively, they may be maintained (e.g., in different compositions and/or containers) and administered separately.

C. Pharmaceutical Packs of Kits

In another aspect, the present invention provides a pharmaceutical pack or kit comprising one or more containers (e.g., vials, ampoules, test tubes, flasks or bottles) containing one or more ingredients of an inventive pharmaceutical composition, allowing administration of a IGFBP-3 polypeptide derivative of the present invention. The present invention also provides a kit comprising one or more containers containing one or more ingredients allowing determination of the concentration of pro-IGF-II in a biological sample. Such a kit will generally comprise an IGFBP-3 polypeptide derivative of the invention comprising, fused thereto, the amino acid sequence of SeAP, and at least one reagent to measure alkaline activity of SeAP.

Different ingredients of a pharmaceutical pack or kit may be supplied in a solid (e.g., lyophilized) or liquid form. Each ingredient will generally be suitable as aliquoted in its respective container or provided in a concentrated form. Packs or kits according to the invention may include media for the reconstitution of lyophilized ingredients. Individual containers of the kits will preferably be maintained in close confinement for commercial sale.

In certain embodiments, a pack or kit includes one or more additional therapeutic agent(s). Optionally associated with the container(s) can be a notice or package insert in the form prescribed by a governmental agency regulating the manufacture, use or sale of pharmaceutical or biological products, which notice reflects approval by the agency of manufacture, use or sale for human administration. The notice of package insert may contain instructions for use of a pharmaceutical composition according to methods of treatment disclosed herein.

An identifier, e.g., a bar code, radio frequency, ID tags, etc., may be present in or on the kit. The identifier can be used, for example, to uniquely identify the kit for purposes of quality control, inventory control, tracking movement between workstations, etc.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data are actually obtained.

Example 1: Preparation of IGFBP-3 Polypeptide Derivatives Construction of Transfer Vectors The following transfer vectors were used in the present study: pDB-3s-H6, pMJ-SeAP and pYM-Fc-IgG1. pDB-3s-H6 is a baculovirus transfer vector for secretory protein expression that was constructed in the inventors' laboratory as previously described (Netchine et al., J. Clin. Endocrinol. Metab., 2009, 94: 3913-3921). Similarly, the pMJ-SeAP and pYM-Fc-IgG1 vectors used to produce secreted fusion proteins with either Alkaline Phosphatase (SeAP) or with the Fc fragment of human IgG1, were also constructed in the inventors' laboratory and have previously been described (Bara et al., Int. J. Cancer, 1998, 75: 767-773; Mahiou et al., Biochem. J., 1998, 330: 1051-1058, which are incorporated herein by reference in their entirety).

All recombinant transfer vectors were constructed after the generation of PCR fragments using primers comprising spacers and appropriate endonucleases restriction sites. To minimize secondary structure formation, these reactions were carried out in 10% dimethylsulfoxide as previously described (Chakrabarti and Schutt, Nucleic Acids Res., 2001, 29: 2377-2381) using a PerkinElmer Life Sciences (Norwalk, Conn.) thermocycler under the following conditions: initial denaturation at 94° C. for 10 minutes, followed by 30 40 second-cycles at 94° C., 60° C. and 72° C.

First, a transfer vector harboring the complete coding sequence of human IGFBP-3 in pDB-3s-H6 downstream of a hexahistidine N-terminal extension was constructed (FIG. 1). The PCR reaction used: 5'-ATC GAA ggc cgt ggg ggc cAG GGC GCG AGC TCG GGG GGC TTG GG-3' (SEQ ID NO: 7) and 5'-Cct cga gTT ATC AGC TGC CCT TGC TCT GCA TGC TGT AGC AGT GCA CGT CCT C-3' (SEQ ID NO: 8) (wherein stop codons are underlined) as sense and antisense primers, respectively; and a plasmid harboring the IGFBP-3 cDNA as template. Restriction sites Sfi1 and Xho1 added in the primers above are presented in lower case. The 815 bp PCR product was digested with Sfi1 and Xho1 restriction endonucleases and ligated into the pDB-3s-H6 transfer vector previously digested with the same enzymes. The ligation product was used to transform electrocompetent E. coli cells. A recombinant plasmid, called pDB-3s-H6-IGFBP-3, was selected after nucleotidic sequencing and co-transfected together with baculoviral DNA in Sf9 cells to produce the corresponding recombinant virus encoding the H6-IGFBP-3 recombinant protein.

Site-Directed Mutagenesis

Site-directed mutagenesis was performed using a mutagenic oligonucleotide and a single stranded DNA template essentially as described previously (Kunkel, Proc. Natl. Acad. Sci. USA, 1985, 82: 488-492) using the "MutaGene® Phagemid in vitro mutagenesis kit version 2" (BioRad). Briefly, transfer vectors pMJ-H6-IGFBP-3 and pDB-3s-H6-IGFBP-3, each containing a M13 replication origin, were used to transform the CJ236 (ung-dut-) mutant strain. A phagemid clone was selected to produce viral particles after infection with the helper phage M13KO7. After extraction, the corresponding single stranded DNA served as template in a polymerization reaction comprising a 5'-phosphorylated mutagenic oligonucleotide, T7 DNA polymerase and T4 DNA ligase as described by Kunkel.

The double-stranded product was used to transform an electrocompetent ung dut proficient E. coli strain. Transformant clones were screened for the presence of the mutation by restriction mapping and nucleotidic sequencing. This approach was used to shorten the intermediary domain of human IGFBP-3 by annealing a single strand IGFBP-3 DNA template to the following mutagenic oligonucleotide: 5'-GGG ACC ATA TTC TGT CTC acc acc aga ccc gcc aga ccc gcc aga ccc gcc acc GCT GAC GGC ACT AGC GTT GAC-3' (SEQ ID NO: 9). In the resulting mutein, the 85 amino acids (Residue 95 to Residue 179) present in the wild type IGFBP-3 central domain, have been replaced by a 15 amino acid spacer, the sequence of which is: NH$_2$-GGGSGGSGGSGGSGG-COOH (SEQ ID NO: 4). The mutated plasmid obtained (pDB-mini-IGFBP-3) served to generate a recombinant baculovirus encoding this IGFBP-3 mutein, called "mini-IGFBP-3", which lacks most of the native central domain.

Once this parent sequence was obtained, a new single stranded DNA template was synthesized and used to generate new mutated mini-IGFBP-3s by site-directed mutagenesis.

One of these mutants was created by eliminating the sequence involved in ALS binding to yield mini-IGFBP-3 ALS⁻. To achieve this goal, the basic amino acids KGRKR (SEQ ID NO: 12) in the C-terminal domain of IGFBP was replaced by the sequence AGGSG (SEQ ID NO: 5) using a pBP-mini-IGFBP-3-derived single stranded template with: CCACACACCAGCAGAAGCCGCCGCTGCCGC-CCGCGGAAGGGCGACACTGCa (SEQ ID NO: 10) mutagenic oligonucleotide.

The same template was used to add at the C-terminal end of the mini-IGFBP-3, the GLNDIFEAQKIEWHE (SEQ ID NO: 16) peptide (Beckett et al., Protein Sci., 1999, 8: 921-929), a substrate for the BirA enzyme (Schatz, Biotechnology, 1993, 11: 1138-1143) in conjunction with the following mutagenic oligonucleotide: CCCCTCGAGTCATT-ATTCGTGCCATTCAATTTTTTGGGCTTCAAA AATGTCGTTCAGG CCGCTGCCCTTGCTCTGC (SEQ ID NO: 11). The protein obtained, -mini-IGFBP-3-avitag, could be enzymatically biotinylated.

Production of Fusion Proteins

To obtain the mini-IGFBP-3 reporter protein, the mini-IGFBP-3 coding sequence was fused to the 3' end of the secreted alkaline phosphatase (SeAP) by excision of mini-IGFBP-3 from the vector pDB-3s-H6-mini-IGFBP-3 obtained after its double digestion with Sfi1 and Xho1 restriction endonucleases and subsequent ligation of the resulting fragment in the pMJ-SeAP vector previously digested with the same enzymes. The resulting recombinant plasmid was used to generate a recombinant baculovirus encoding the reporter fusion protein called "SeAP-mini-IGFBP-3".

To obtain the "mini-IGFBP-3 immunoadhesin" fusion protein, joining mini-IGFBP-3 to the Fc fragment of human IgG1, mini-IGFBP-3 amplicons comprising the proper restriction sites were generated by PCR and ligated to the pYM-FcgG1 vector properly digested. The resulting recombinant plasmid was used to generate a recombinant baculovirus encoding the immunoadhesin fusion protein called "IGFBP-3-Fc".

Purification of Recombinant Proteins

The culture medium of insect cells infected with any of the recombinant viruses described above was harvested and the recombinant protein was purified by IMAC essentially as previously described (Mahiou et al., 1998—see above). Since recombinant proteins required an additional purification step by ion-exchange chromatography: IGFBP-3-Fc immunoadhesin was further purified by protein-A-Sepharose affinity chromatography (Mahiou et al., 1998—see above).

Example 2: Properties of Mini-IGFBP-3

Figure 2:
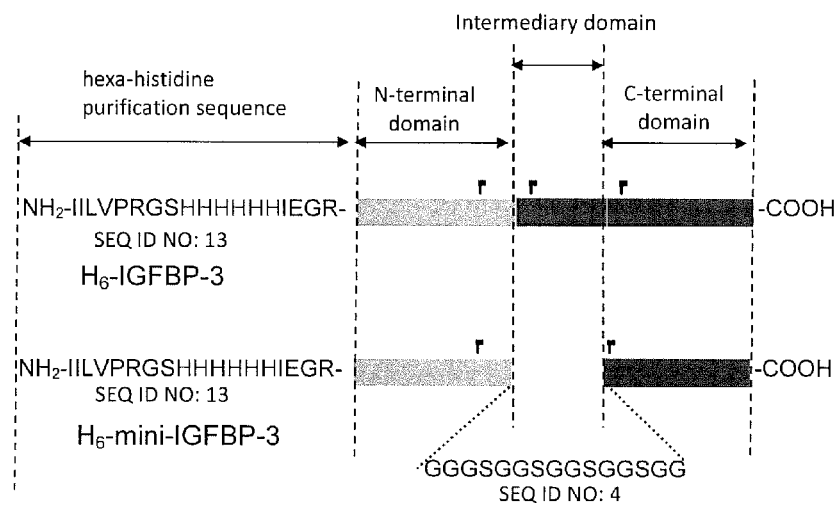
FIG. 2(A) is a schematic representation of wild-type (H6-IGFBP-3) and mutated recombinant IGFBP-3 (mini-IGFBP-3).
FIG. 2(B) shows an alignment of the amino acid sequences of H6-IGFBP-3 and mini-IGFBP-3 mutein. The hexa-histidine purification sequence, the N-terminal domain, the intermediate domain, and the C-terminal domain are presented and the potential N-glycosylation sites are symbolized by flags.

FIG. 2 shows a schematic representation of wild type IGFBP-3 (H6-IGFBP-3) and of mutated recombinant IGFBP-3 (mini-IGFBP-3), illustrating the fact that the latter derives from wild-type H6-IGFBP-3 by replacement of most of its intermediate domain by the indicated 15 amino-acid flexible linker achieved by site-directed mutagenesis. Also presented on FIG. 2 are the amino acid sequences of H6-IGFBP-3 and mini-IGFBP-3.

Binding Properties.

Figure 3:
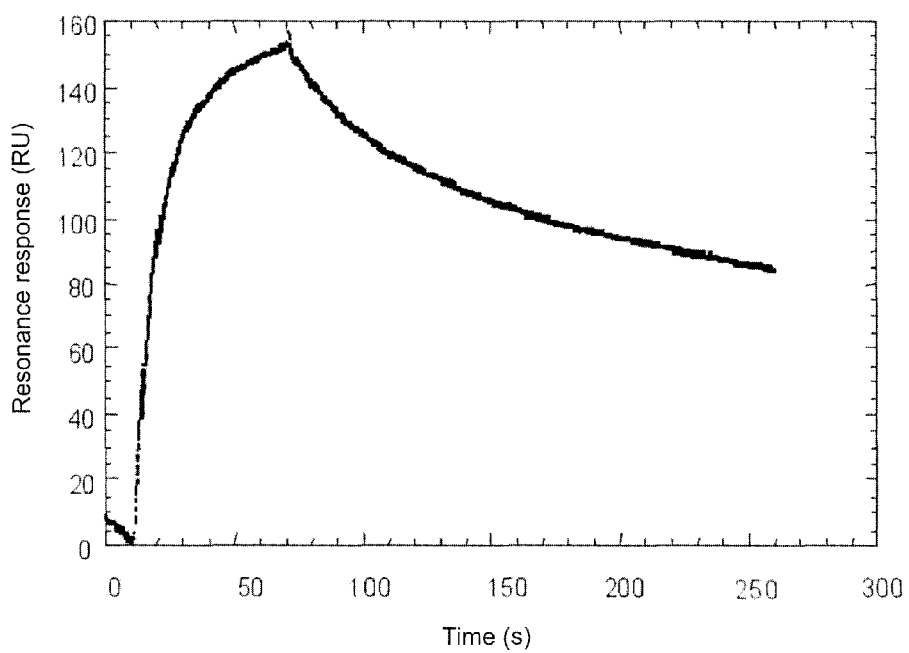
FIG. 3 is a graph showing the kinetics of association and dissociation of the mini-IGFBP-3/IGF-II complex analyzed by surface Plasmon resonance (see Example 2 for experimental details).

The kinetics of association and dissociation of mini-IGFBP-3 and IGF-II was studied by surface Plasmon resonance (BIAcore). Mini-IGFBP-3 was covalently coupled to a CM-5 surface via carbodiimide. After saturation with a 1M ethanolamine solution, a solution of IGF-II in PBS was injected on the surface, and this was replaced by buffer after 80 seconds. The results obtained are presented on FIG. 3.

The affinity of wild type (wt) IGFBP-3 and of mutated IGFBP-3 (mini-IGFBP-3) for IGF-I and IGF II was determined using $^{125}$I-IGF-1 as a radioactive tracer. Various concentrations of IGF-I and IGF-II were used as competitors and affinity constants were determined by Scatchard analysis. The results obtained are presented in the following table.

TABLE 1 wild type (wt) IGFBP-3 and of mutated IGFBP-3
(mini-IGFBP-3) for IGF-I and IGF II

|  | IGF-I | IGF-II |
|---|---|---|
| wt IGFBP-3 | $2.96 \times 10^{10}$ $M^{-1}$ | $3.50 \times 10^{10}$ $M^{-1}$ |
| mini-IGFBP-3 | $2.40 \times 10^{10}$ $M^{-1}$ | $3.14 \times 10^{10}$ $M^{-1}$ |

Resistance of Mini-IGFBP-3 to Proteolytic Degradation.

Figure 4:
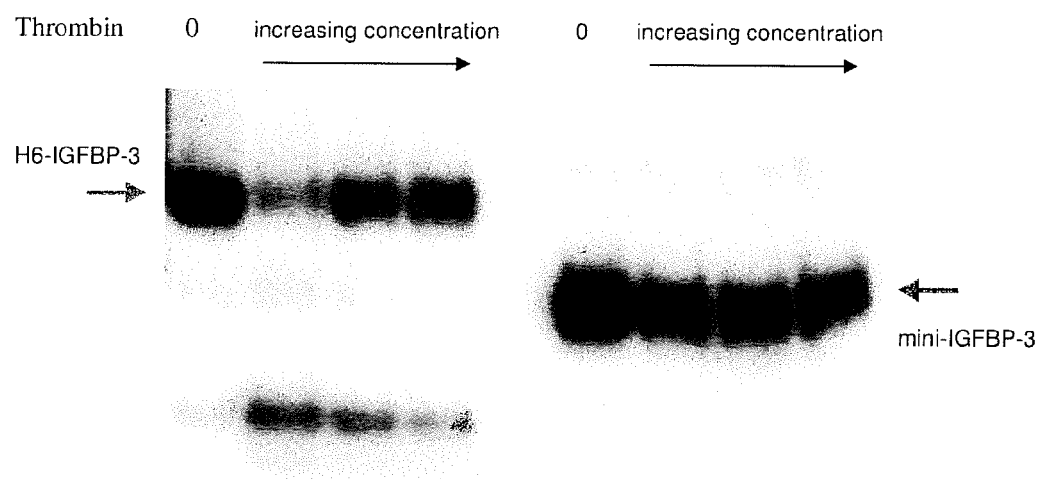
FIG. 4 presents gels showing the susceptibility of wild type IGFBP-3 (left) and of mini-IGFBP-3 (right) to proteolytic degradation by thrombin (see Example 2 for experimental details).

The susceptibility of wild type IGFBP-3 and of mini-IGFBP-3 to proteolytic degradation by thrombin was studied by incubating the purified proteins (100 ng) with increasing concentrations of thrombin (0.0008; 0.004; 0.02 and 0.1 NHI U/mL) for one hour. Digestion products were then separated by SDS-PAGE, transferred to PVDF membranes and analyzed by immunoblot using a rabbit polyclonal antibody raised against the entire IGFBP-3 molecule. The results obtained are presented on FIG. 4.

Example 3: Properties of Mini-IGFBP-3-Avitag

Figure 5:
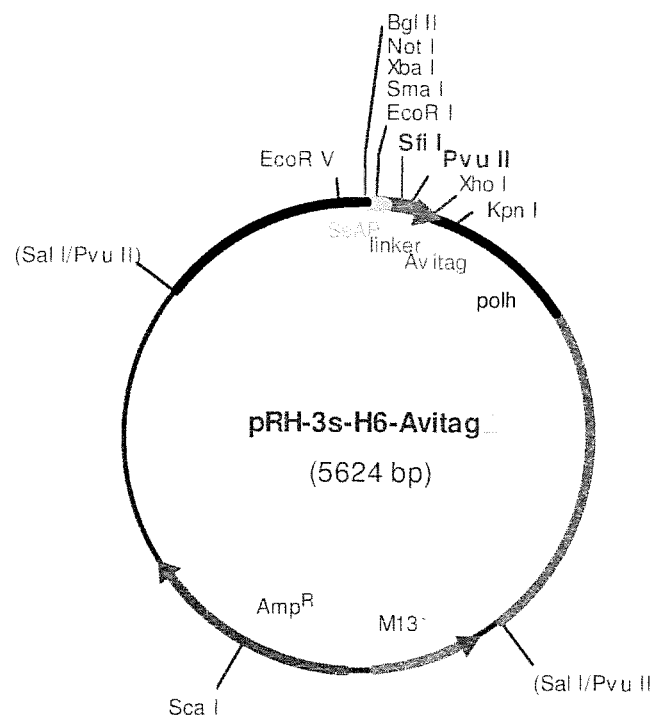
FIG. 5 shows a restriction map of the pRH-3s-avitag transfer vector obtained by site-directed mutagenesis and in which the coding sequence of mini-IGFBP-3 has been inserted to produce sequentially the pRH-3s-H6-mini-IGFBP-3 vector, the AcMNPV-mini-IGFBP-3 recombinant virus and the mini-IGFBP-3-avitag recombinant protein.

FIG. 5 shows a schematic representation of a restriction map of the pRH-3s-H6-avitag transfer vector obtained by site-directed mutagenesis. In this vector, any open reading frame sequence flanked by Sfi I and Pvu II restriction sites can be introduced by PCR in the vector digested by the same enzymes. The secreted polypeptide resulting from the translation of the construct will carry the Avitag peptide at its C-terminal end and will be amenable to targeted enzymatic biotinylation using BirA enzyme. The coding sequence of mini-IGFBP-3 was introduced in this vector yielding sequentially, the pRH-3s-H6-mini-IGFBP-3 vector, the AcMNPV-mini-IGFBP-3 recombinant virus and the mini-IGFBP-3-avitag recombinant protein.
Enzymatic Biotinylation of Mini-IGFBP-3-Avitag.

Figure 6:
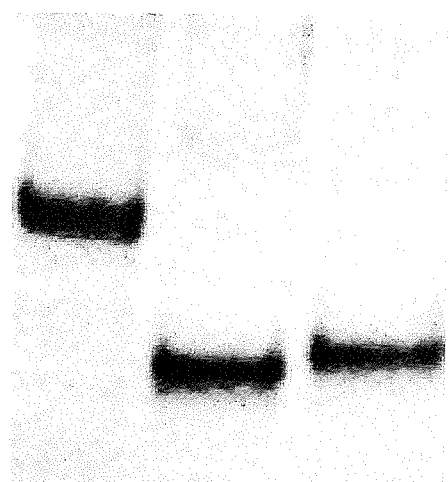
FIG. 6 shows the results of an electrophoretic analysis of recombinant mini-IGFBP-3-Avitag after targeted enzymatic biotinylation. Left panel: Purified recombinant H6-IGFBP-3 (A), mini-IGFBP-3 (B) mini-IGFBP-3-Avitag (C) were analyzed by SDS-PAGE and stained with Coomassie Brilliant Blue. Right panel: purified mini-IGFBP-3-Avitag was submitted to biotinylation with biotin and the BirA enzyme, and an aliquot of the reaction product was loaded onto an SDS-PAGE (E) side by side with a monoclonal antibody (7E8) previously chemically biotinylated (D). See Example 3 for experimental details.
Figure 6:
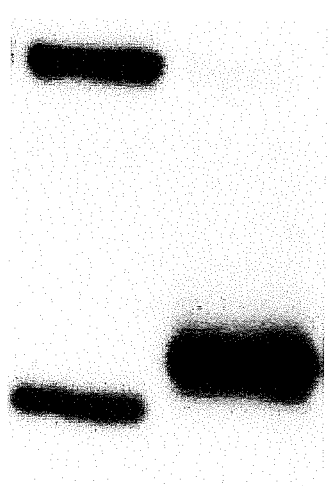

To assess the susceptibility of mini-IGFBP-3-Avitag to enzymatic biotinylation, purified recombinant H6-IGFBP-3, mini-IGFBP-3 and mini-IGFBP-3-Avitag (1 µg of each) were analyzed by SDS-PAGE and stained with Coomassie Brilliant Blue. Mini-IGFBP-3-Avitag was first purified before being added to a biotinylation reaction mixture containing biotin and the BirA enzyme. An aliquot of the reaction product was loaded onto an SDS-PAGE side by side with a monoclonal antibody (7E8) which had previously been chemically biotinylated. The gel was transferred onto a PVDF membrane which, after saturation, was incubated with Streptavidin-HRP. The peroxidase activity was determined by chemiluminescence. The results obtained are presented on FIG. 6.
Targeted Enzymatic Biotinylation of Mini-IGFBP-3-Avitag in Crude Extracts.

Figure 7:
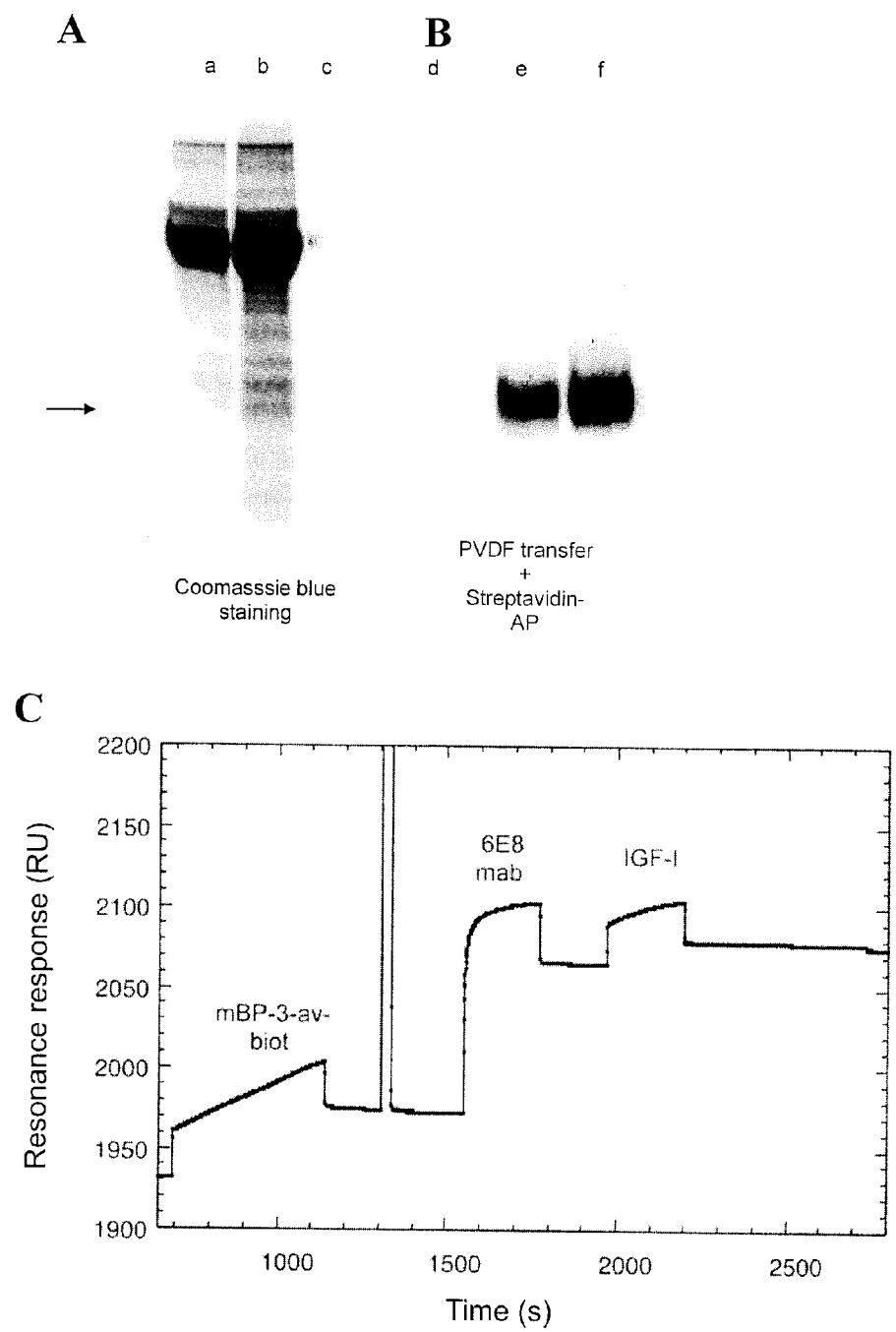
FIG. 7(A) shows the electrophoretic analysis of different protein extracts from (a) culture supernatant of Sf-9 cells infected by a virus producing parental mini-IGFBP-3, (b) culture supernatant of Sf-9 cells infected by a virus producing mini-IGFBP-3-avitag, and (c) purified mini-IGFBP-3-avitag.
FIG. 7(B) shows the electrophoretic analysis of the protein extracts after targeted BirA biotinylation, separation by SDS-PAGE, transfer onto a PVDF membrane, incubation with Streptavidin-AP and of APase activity by addition of NBT/BCIP. Lanes c, d and e correspond to biotinylated lanes a, b, and c, respectively.
In FIG. 7(C), after extensive dialysis against PBS, the crude culture medium containing mini-IGFBP-3-avitag-biotin (lane e) was injected on a Streptavidin chip. After washing with 1 M NaCl, a solution containing the 6E8 anti-IGFBP-3 monoclonal antibody and a solution containing IGF-II were sequentially injected.

Protein extracts from (a) a supernatant of a culture of Sf-9 cells infected by a virus producing parental mini-IGFBP-3, (b) a supernatant of a culture of Sf-9 cells infected by a virus producing mini-IGFBP-3-Avitag, and (c) purified mini-IGFBP-3-avitag were submitted to targeted BirA biotinylation. An aliquot of each of the samples was then separated by SDS-PAGE and then transferred onto a PVDF membrane, which was then incubated with Streptavidin-AP. APase activity was then demonstrated by adding NBT/BCIP. The results obtained are presented on FIG. 7.

After extensive dialysis against PBS, the crude culture medium containing mini-IGFBP-3-avitag-biotin (lane e in panel B of FIG. 7) was injected on a Streptavidin chip. After washing with 1M NaCl, a solution containing the 6E8 anti-IGFBP-3 monoclonal antibody and a solution containing IGF-II were sequentially injected. The results obtained are presented on FIG. 7(C).

Example 4: SeAP-Mini-IGFBP-3 Reporter Fusion Protein and Uses Thereof

Figure 8:
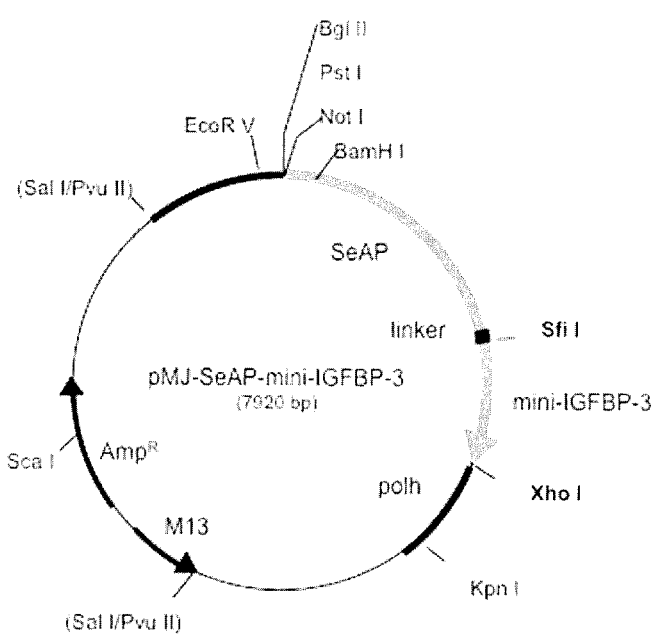
FIG. 8(A) shows the restriction map of the pMJ-SeAP-mini-IGFBP-3 transfer vector constructed to produce the SeAP-mini-IGFBP-3 reporter fusion protein.
FIG. 8(B) is a schematic representation of the solid phase "sandwich" assay developed to determine pro-IGF-II concentrations in human plasma.
FIG. 8(C) is a graph showing the pro-IGF-II levels determined using the "sandwich" assay in the plasma of healthy adults, patients with islet cell tumor hypoglycaemia (NICTH) and patients with NICTH after tumor removal. See Example 4 for experimental details.
Figure 8:
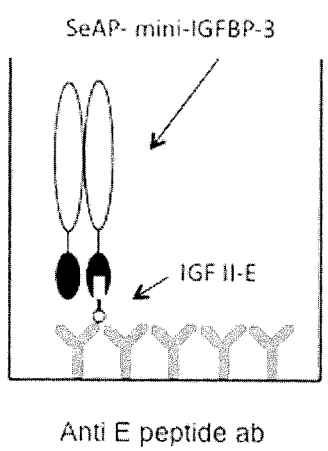
Figure 8:
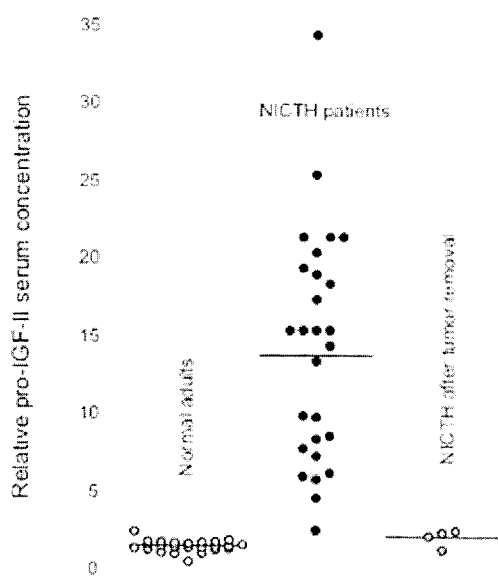

FIG. 8(A) shows the restriction map of the pMJ-SeAP-mini-IGFBP-3 transfer vector constructed and used to produce the SeAP-mini-IGFBP-3 reporter fusion protein.
Solid-Phase Sandwich Assay.

A schematic representation of a solid-phase "sandwich" assay developed to determine pro-IGF-II concentrations in human plasma is presented on FIG. 8(B). This "sandwich" assay uses as capture reagent a polyclonal anti-IGF-II E-peptide antibody immobilized on a support and as specific reporter reagent, SeAP-mini-IGFBP-3.

This assay was validated by determining pro-IGF-II levels in the plasma of healthy adults (n=40), of patients diagnosed with non-islet cell tumor hypoglycaemia (NICTH) (n=25), and of patients with NICTH after tumor removal (n=4). The results obtained are presented on FIG. 8(C).

Example 5: Properties of Mini-IGFBP-3-Fc

Figure 9:
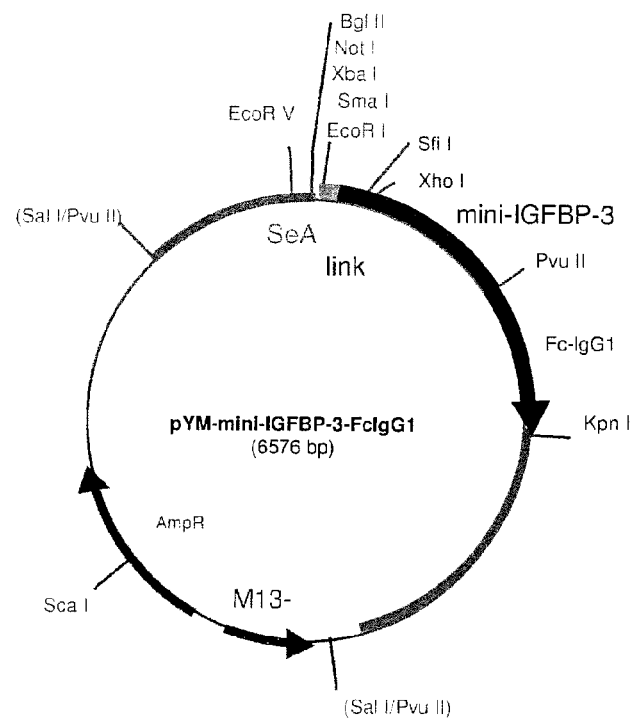
FIG. 9(A) shows the restriction map of the pYM-mini-IGFBP-3 transfer vector constructed to produce the mini-IGFBP-3-FcIgG1 fusion protein.
FIG. 9(B) is a schematic representation of the resulting immunoadhesin.
Figure 9:
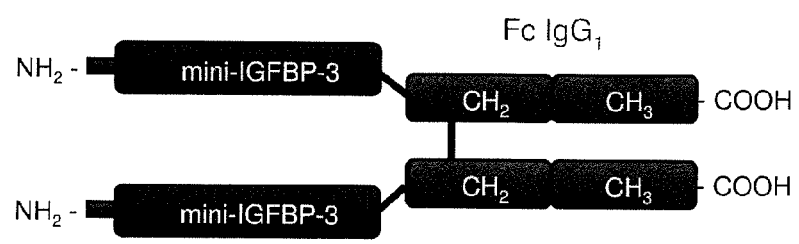

FIG. 9(A) shows the restriction map of the pYM-mini-IGFBP-3 transfer vector constructed used to produce the mini-IGFBP-3-FcIgG1 fusion protein, which is schematically represented on FIG. 9(B).
Affinity of Mini-IGFBP-3-Fc for IGF-II.

Figure 10:
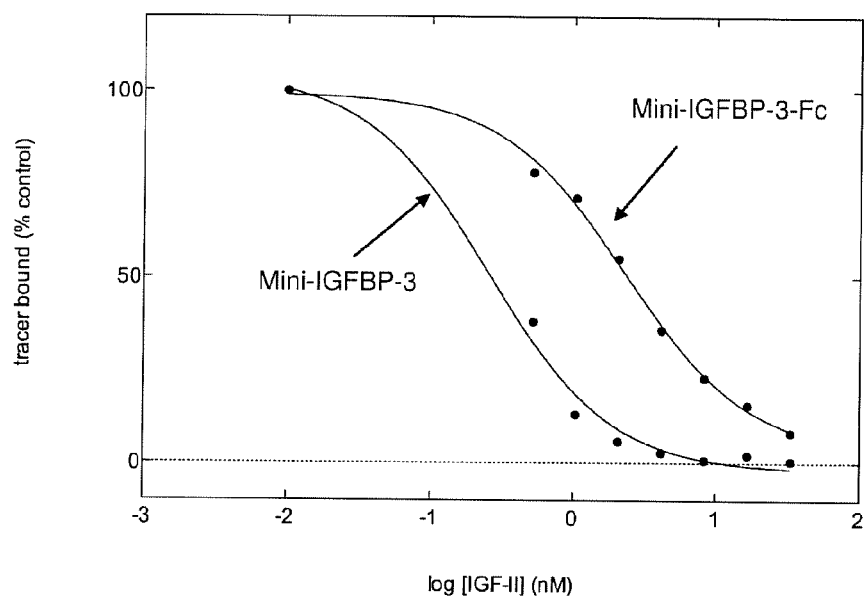
FIG. 10(A) is a graph showing the relative binding affinity of mini-IGFBP-3 and mini-IGFBP-3-Fc towards IGF-II. The solid phase assay used measured the ability of increasing concentrations of free IGF-II to displace binding of the biotinylated IGF-II tracer to mini-IGFBP-3 and mini-IGFBP-3-Fc immobilized on a support (See Example 5 for experimental details).
FIG. 10(B) is a graph showing the effects of mini-IGFBP-3-Fc on proliferation and survival of three human tumor cell lines cultivated in the presence of 10% FCS: Hep3B, HuH7 and INA-6. The effects of mini-IGFBP-3-Fc are compared to the effects of picropodophyllin (ppp), a compound known to interfere with IGF-R signalling pathway (see Example 5 for experimental details).
Figure 10:
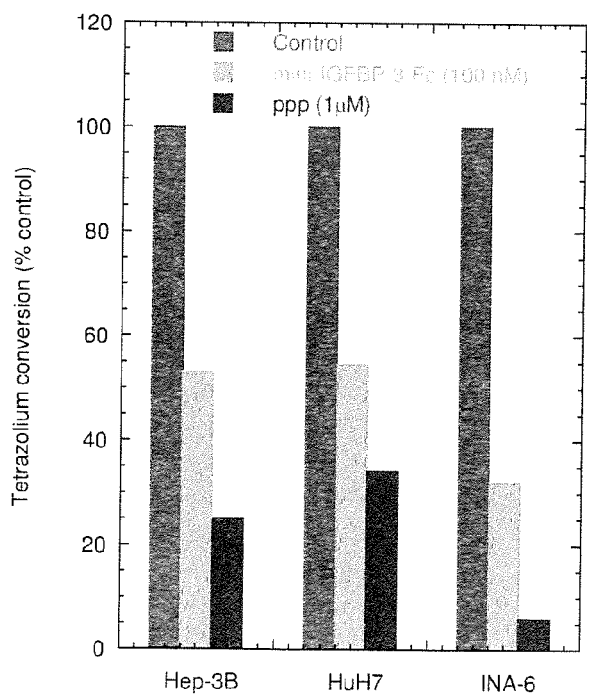

A solid-phase assay was used to study the binding affinity of mini-IGFBP-3-Fc for IGF-II. In this assay, two binding proteins (mini-IGFBP-3 and mini-IGFBP-3-Fc) were immobilized to a support. They were incubated with the biotinylated IGF-II tracer, and then increasing concentrations of IGF-II were added. The results obtained, which are presented on FIG. 10(A), show that mini-IGFBP-3-Fc bind IGF-II with higher apparent affinity that its unfused counterpart (mini-IGFBP-3).
Anti-Proliferative Activity of Mini-IGFBP-3-Fc.

The effects of mini-IGFBP-3-Fc on the proliferation and survival of three human tumor cell lines, Hep3B and HuH7—hepatocellular carcinoma cell lines) and INA-6 (multiple myeloma cell line), were studied. For each cell line cultivated in the presence of 10% fetal calf serum (FCS), the effect of mini-IGFBP-3-Fc were compared to the effect picropodophyllin (ppp), a compound known to interfere with the IGF1-R signalling pathway. A cell viability assay was performed 72 hours after initiation of the culture in the presence of mini-IGFVP-3-Fc (100 nM) or ppp (1 µM) in a medium containing 10% FCS by adding WST-1 and monitoring formazan conversion. The results obtained are presented in FIG. 10B). They show that mini-IGFBP-3-Fc has anti-proliferative activity on the three human tumor cell lines tested.
AKT-Phosphorylation Inhibition by Mini-IGFBP-3-Fc.

Figure 11:
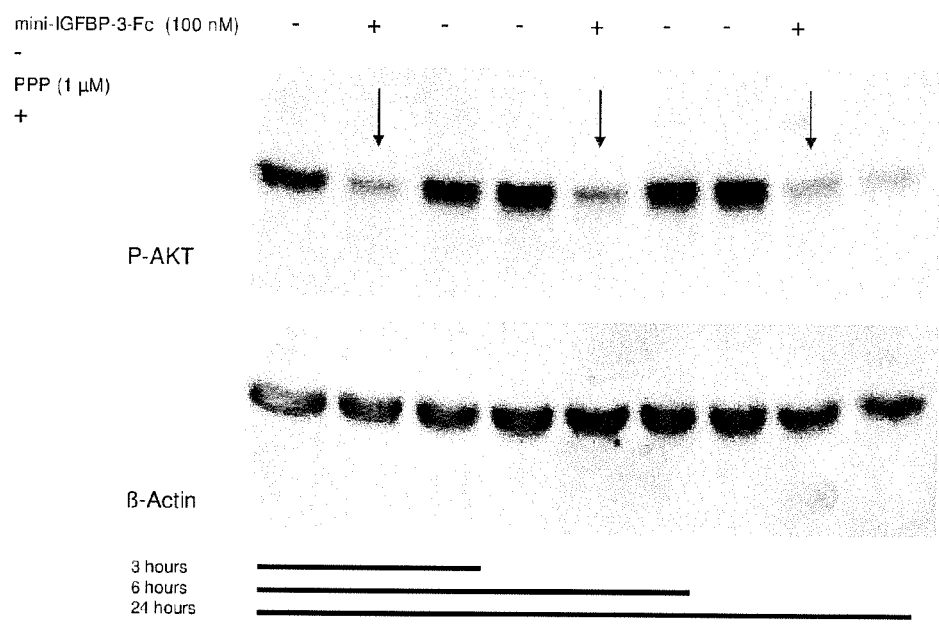
FIG. 11(A) shows the inhibiting effects of mini-IGFBP-3-Fc on the phosphorylation of AKT in INA-6 myeloma cells. These effects are compared to those of ppp (see Example 5 for experimental details).
FIG. 11(B) is a graph showing the effects of mini-IGFBP-3-Fc on the phosphorylation of AKT in MiaPaCa-2 cells (upper left), HT-29 cells (upper right) and A549 cells (lower left) and of mini-IGFBP-3-Fc on the phosphorylation of AKT in A549 cells (lower right) after different incubation times, as indicated (see Example 5 for experimental details).
Figure 11:
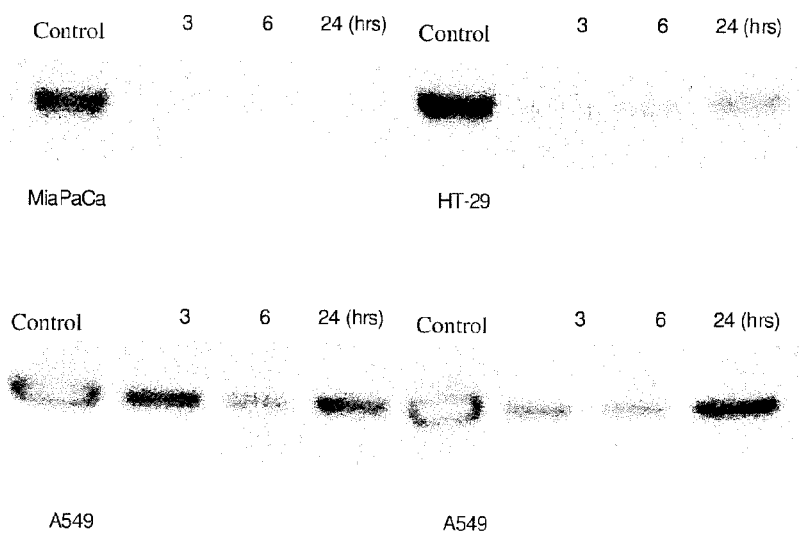

The INA-6 myeloma cell line was grown in the presence of 10% FCS. The cells were incubated with mini-IGFBP-3 (100 nm) or ppp (1 µM) 3, 6 or 24 hours. After incubation, the cells were lysed using a lysis buffer, and cell extracts (normalized for protein contents) were loaded on SDS-PAGE gel, transferred onto nitrocellulose membrane, which was further incubated with a monoclonal antibody directed against the phospho-S273 residue of the AKT protein. The membrane was also re-probed after stripping with an antiactin antibody to check for equal loading. The results obtained are presented in FIG. 11A).

The inhibiting activity of mini-IGFBP-3-Fc on AKT phosphorylation was also assessed in various human tumor cell lines: MiaPaCa-2 (pancreatic cancer), HT-29 (colon cancer) and A549 (lung cancer). The inhibiting activity of mini-IGFBP-3 on AKT phosphorylation was assessed A549 cells. The results, obtained, which are presented on FIG. 11B), show that mini-IGFBP-3-Fc and mini-IGFBP-3 are able to block the AKT phosphorylation of all the human tumor cell lines tested.

Example 6: Properties of Mini-IGFBP-3 and Derivatives In Vivo

To pave the ground for future assessments of mini-IGFBP-3 in vivo activity, mini-IGFBP-3 and its derivatives were injected into mice. When measured using human-specific IGFBP-3 ELISA test, several kinetics could be observed.

Figure 12:
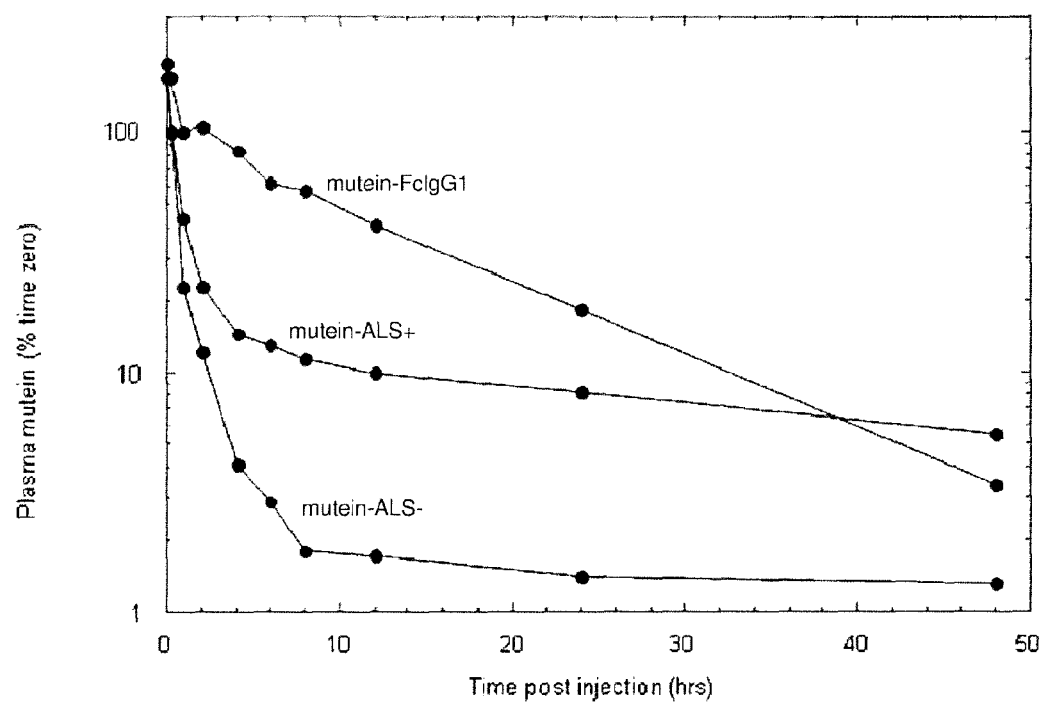
FIG. 12 shows the decay of mini-IGFBP-3 derivatives concentrations in mouse plasma. 250 µg of the indicated protein were injected intravenously to groups (n=3) of mice at time zero. Blood samples were drawn at the indicated time points, centrifuged and kept frozen. Concentrations of injected proteins were determined by an in-house sandwich type ELISA using anti-human IGFBP-3 specific monoclonal antibodies.

As seen on FIG. 12, after administration, mini-IGFBP-3 cleared from the bloodstream with two different kinetics: 80-90% of the initial dose left the bloodstream in the first 3-4 hours while the remaining 10-20% disappeared very slowly until 48 hours. As expected, mini-IGFBP-3 bearing the mutation suppressing binding to ALS disappeared much faster with almost no protein remaining 8 hours after injection. In contrast, mini-IGFBP-3-Fc serum concentration decayed with much slower single slope kinetics with a half-life of about 12 hours.

The IGF-II producing HT-29 human colon adenocarcinoma cell line, which had previously been shown to be responsive to mini-IGFBP-3 in vitro, was used to assess mini-IGFBP-3 in vivo activity. Thus, HT-29 xenografts were established in nude mice. After tumor had reached a critical size, mice were treated with either mini-IGFBP-3 or mini-IGFBP3-Fc in three i.p. injections separated by a three hours interval and mice were sacrificed after 3 additional hours. Tumor MEK and PI3Kinase signalling pathways were assessed in these tumors, together with the cell cycle regulator Rb, by evaluating the phosphorylation status of AKT, ERK-1/2 and Rb, respectively, using western immunoblots.

More specifically, $2.5 \times 10^6$ HT-29 cells were injected s.c. into each flank of 5 weeks old NMRI-nu mice. Tumors were allowed to grow up to a volume of 500 $mm^3$ before mice were randomized into individual treatment groups (n=2) and received three i.p. injections (340 µg) of either mini-IGFBP-3 or mini-IGFBP-3-Fc every 3 hours. The control group was injected with saline. Twelve (12) hours after treatment initiation, mice were sacrificed and excised tumors were cut in half. One half was snap frozen in liquid nitrogen and stored at −80° C. The other half was fixed in Finfix, included in paraffin and processed for immuno-histochemistry. For Western blot analysis, tumors were homogenized in lysis buffer (10 mM Tris HCl at pH 7.4, 150 mM NaCl, 1% Nonidet P-40, 0.1% sodium deoxycholate, 0.1% SDS, 1 mM EDTA, 2 mM sodium orthovanadate, protease inhibitor tablet [Roche Molecular Biochemicals]). After centrifugation, protein concentrations were determined by the Bio-Rad protein assay (Bio-Rad). Fifteen micrograms of protein were run on a 4%-12% SDS-PAGE gel (Invitrogen). Membranes were blocked in 5% nonfat milk in TBS-T overnight at 4° C., washed with TBS-T, incubated with anti-mouse or anti-rabbit horseradish peroxidase-conjugated secondary antibodies in TBS-T for 1 hour at room temperature, and washed in TBS-T. The signal was visualized using an enhanced chemiluminescence solution and exposed to film. The blotting antibodies used wherein phosphor-Akt, Akt, mitogen-activated protein kinase ERK1/2, phosphor-mitogen-activated protein kinase pErk1/2, Rb (BD Biosciences), β-actin and G3PDH; antibodies were from Cell Signalling Technology unless otherwise stated.

Figure 13:
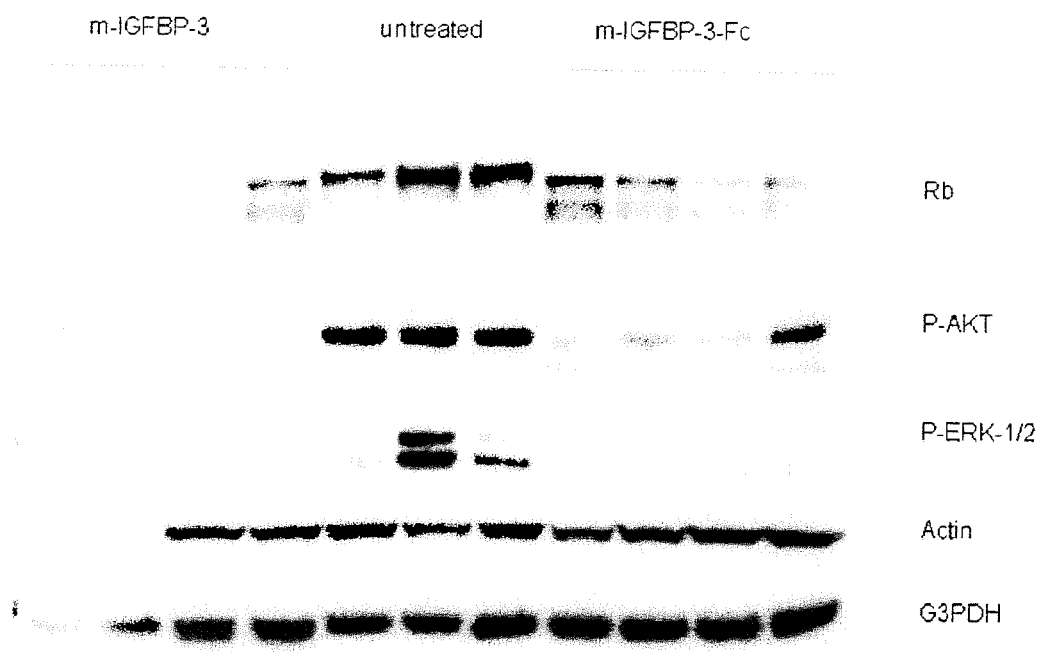
FIG. 13 shows the in vivo effects on tumor key signalling parameters of a 12 hours treatment with mini-IGFBP-3 or mini-IGFBP-Fc administered to mice bearing HT-29 human colorectal tumor xenografts. (See Example 6 for experimental details).

As seen on FIG. 13, a 12 hours treatment with either mini-IGFBP-3 or mini-IGFBP-3-Fc, abolished AktS473 phosphorylation in tumors from each treated mouse indicating a strong blockade of PI3K signalling pathway. As expected, the MEK signalling pathway was similarly interrupted since Erk1/2 phosphorylation was also considerably decreased in treated tumors as compared to their untreated counterparts. Thus, the cell cycle control was assessed by examining the phosphorylation status of the Rb protein. As shown on FIG. 13, while the Rb protein was fully phosphorylated in untreated tumors, Rb phosphorylation decreased in all treated tumors. In line with these data, mitotic index was slightly lower (−12%) in these tumors as compared to their untreated counterpart. Altogether, these data indicate that mini-IGFBP-3 and its derivative mini-IGFBP-3-Fc are both active in vivo to interrupt the two main signalling pathways activated by either IGF-1R or IR-A Receptor Tyrosine Kinases leading to initiation of cell cycle arrest. Thus, sequestration of free IGF-I and free IGF-II in an animal carrying an IGF-II producing tumor by a protease-resistant IGF binding protein depletes bioavailable IGFs to the tumor so as to starve the tumor and block signalling pathways involved in tumor cell cycle progression. Treatment duration used in these experiments was too short to observe activation of apoptosis-linked markers.

Example 7: Present and Future Work

The ability of mini-IGFBP-3 to prevent the emergence of cells escaping their dependence on estrogen is currently being treated. MCF-7 cells typical of Luminal A type of neoplasia are estrogen receptor positive and depend on estrogen for their multiplication. In these experiments, these cells are plated in estrogen-depleted medium in the presence or absence of mini-IGFBP-3. Estrogen-independent growth is assessed in control and test plates by staining with crystal violet. Whereas some control cells grow under those conditions, no cell is expected to grow in mini-IGFBP-3-treated plates.

The ability of mini-IGFBP-3 to resist proteolytic digestion by Matrix Metalloproteinases, MMP-7 and MMP-9, is also currently being tested. MMP-7 and MMP-9 are expressed by tumor cells and are present in higher quantity in the bloodstream of cancer patients where they contribute to the degradation of native, endogenous IGFBP-3. In the experiments, these enzymes are first activated with 1 mM APMA. Mini-IGFBP-3 and full length IGFBP-3 are compared as substrate for activated MMP-7 and MMP-9. Concentrations of each substrate (20 µM) are incubated in a 1:10 molar ratio with either MMP-7 or MMP-9. At the end of the incubation period, proteins are analyzed by SDS-PAGE to evaluate their respective cleavage into fragments. Whereas, full-length IGFBP-3 is digested by both MMP-7 and MMP-9, mini-IGFBP-3 resists this proteolytic attack.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. An insulin-like growth factor binding protein 3 (IGFBP-3) polypeptide derivative comprising an N-terminal domain, an intermediary domain and a C-terminal domain, wherein:
   the N-terminal domain comprises the amino acid sequence of the N-terminal domain of wild-type human IGFBP-3;
   the intermediary domain (i) consists of a linker consisting of the amino acid sequence set forth in SEQ ID NO: 4, or (ii) comprises the amino acid sequence of the intermediary domain of wild-type human IGFBP-3, wherein 85 or more than 85 contiguous amino acid residues of said amino acid sequence are replaced with a linker consisting of the amino acid sequence set forth in SEQ ID NO: 4; and
   the C-terminal domain comprises the amino acid sequence of the C-terminal domain of wild-type IGFBP-3, or of a biologically active fragment thereof that retains the ability of the C terminal domain of wild type human IGFBP 3 to bind to IGF I, IGF II, heparin and ALS.

2. The IGFBP-3 polypeptide derivative according to claim 1, wherein: the intermediary domain of the IGFBP-3 polypeptide derivative comprises the amino acid sequence of the intermediary domain of wild-type IGFBP-3 set forth in SEQ ID NO: 2, wherein 85 or more than 85 contiguous amino acid residues of said amino acid sequence are replaced with a linker consisting of the amino acid sequence set forth in SEQ ID NO: 4.

3. The IGFBP-3 polypeptide derivative according to claim 1, wherein:
   the amino acid sequence of the N-terminal domain of wild-type human IGFBP-3 is as set forth in SEQ ID NO: 1; and
   the amino acid sequence of the C-terminal domain of wild-type human IGFBP-3 is as set forth in SEQ ID NO: 3.

4. The IGFBP-3 polypeptide derivative according to claim 3, wherein amino acid residues 43 to 47 in SEQ ID NO: 3 are replaced with AGGSG (SEQ ID NO: 5).

5. The IGFBP-3 polypeptide derivative according to claim 1 further comprising, fused thereto, the immunoglobulin IgG1 Fc fragment.

6. The IGFBP-3 polypeptide derivative according to claim 1 further comprising the amino acid sequence of insulin-like growth factor 1 (IGF-I), wherein the IGF-I is complexed to the IGFBP-3 polypeptide derivative.

7. The IGFBP-3 polypeptide derivative according to claim 1 further comprising a BirA enzyme substrate covalently bound to the terminal end of the C-terminal domain of the IGFBP-3 polypeptide derivative.

8. The IGFBP-3 polypeptide derivative according to claim 7, wherein the BirA enzyme substrate has the sequence set forth in SEQ ID NO: 6.

9. The IGFBP-3 polypeptide derivative according to claim 7 further comprising biotin covalently bound to the BirA enzyme substrate.

10. The IGFBP-3 polypeptide derivative according to claim 1 further comprising, fused thereto, the amino acid sequence of SeAP (secreted alkaline phosphatase).

11. The IGFBP-3 polypeptide derivative according to claim 3, wherein amino acid residues 43 to 47 in SEQ ID NO: 3 are replaced with AGGSG (SEQ ID NO: 5).

12. The IGFBP-3 polypeptide derivative according to claim 8 further comprising biotin covalently bound to the BirA enzyme substrate.

13. The IGFBP-3 polypeptide derivative according to claim 2, wherein:
   the amino acid sequence of the N-terminal domain of wild-type human IGFBP-3 is as set forth in SEQ ID NO: 1; and
   the amino acid sequence of the C-terminal domain of wild-type human IGFBP-3 is as set forth in SEQ ID NO: 3.

14. A pharmaceutical composition comprising a therapeutically effective amount of at least one IGFBP-3 polypeptide derivative according to claim 1 and a pharmaceutically acceptable carrier or excipient.

15. A pharmaceutical composition comprising a therapeutically effective amount of at least one IGFBP-3 polypeptide derivative according to claim 6 and a pharmaceutically acceptable carrier or excipient.

16. A kit comprising an IGFBP-3 polypeptide derivative according to claim 10 and at least one reagent to measure alkaline activity.

17. A method for determining pro-IGF-II concentration in a biological sample, the method comprising steps of:
   contacting the biological sample with an IGFBP-3 polypeptide derivative according to claim 10 so as to allow formation of a complex between the IGFBP-3 polypeptide derivative and any pro-IGF-II present in the biological sample, wherein pro-IGF-II is a partially processed form of IGF-II; and
   determining the concentration of pro-IGF-II in the biological sample by measuring the alkaline activity of SeAP in the complex.

* * * * *